US008636995B2

(12) United States Patent
Stolen

(10) Patent No.: US 8,636,995 B2
(45) Date of Patent: Jan. 28, 2014

(54) METHODS AND DEVICES TO REGULATE STEM CELL HOMING

(75) Inventor: Craig Stolen, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 546 days.

(21) Appl. No.: 11/469,092

(22) Filed: Aug. 31, 2006

(65) Prior Publication Data

US 2008/0057027 A1 Mar. 6, 2008

(51) Int. Cl.
*A61K 35/12* (2006.01)
*A01N 1/02* (2006.01)
*A61K 38/19* (2006.01)

(52) U.S. Cl.
USPC .... 424/85.1; 424/93.21; 424/93.7; 435/284.1

(58) Field of Classification Search
None
See application file for complete search history.

(56) References Cited

U.S. PATENT DOCUMENTS

| | | | |
|---|---|---|---|
| 3,923,794 A | 12/1975 | Maruyama et al. | |
| 4,676,980 A | 6/1987 | Segal et al. | |
| 5,196,403 A | 3/1993 | Maraganore et al. | |
| 5,474,563 A | 12/1995 | Myler et al. | |
| 5,512,442 A | 4/1996 | Jalkanen et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,580,780 A | 12/1996 | Jalkanen et al. | |
| 5,585,089 A | 12/1996 | Queen et al. | |
| 5,611,016 A | 3/1997 | Fangmann et al. | |
| 5,625,126 A | 4/1997 | Lonberg et al. | |
| 5,633,425 A | 5/1997 | Lonberg et al. | |
| 5,691,423 A | 11/1997 | Smith et al. | |
| 5,718,892 A | 2/1998 | Keefer et al. | |
| 5,736,137 A | 4/1998 | Anderson et al. | |
| 5,776,456 A | 7/1998 | Anderson et al. | |
| 5,843,439 A | 12/1998 | Anderson et al. | |
| 5,935,598 A | 8/1999 | Sage et al. | |
| 5,961,483 A | 10/1999 | Sage et al. | |
| 6,066,321 A | 5/2000 | Jalkanen et al. | |
| 6,152,141 A | 11/2000 | Stevens et al. | |
| 6,185,953 B1 | 2/2001 | Sada et al. | |
| 6,203,788 B1 | 3/2001 | Blaschuk et al. | |
| 6,214,334 B1 | 4/2001 | Lee et al. | |
| 6,261,549 B1 | 7/2001 | Fernandez et al. | |
| 6,399,061 B1 | 6/2002 | Anderson et al. | |
| 6,461,821 B1 | 10/2002 | Matsuzawa et al. | |
| 6,541,116 B2 | 4/2003 | Michal et al. | |
| 6,569,996 B1 | 5/2003 | Blaschuk et al. | |
| 6,571,125 B2 | 5/2003 | Thompson | |
| 6,586,187 B1 | 7/2003 | Gopalsamy et al. | |
| 6,624,202 B2 | 9/2003 | Smith et al. | |
| 6,663,863 B2 | 12/2003 | Horvath et al. | |
| 6,667,034 B2 | 12/2003 | Palsson et al. | |
| 6,682,734 B1 | 1/2004 | Anderson et al. | |
| 6,806,255 B2 | 10/2004 | Doherty et al. | |
| 6,907,238 B2 | 6/2005 | Leung | |
| 6,914,144 B2 | 7/2005 | Pye | |
| 6,962,969 B2 | 11/2005 | Blaschuk et al. | |
| 6,982,286 B2 | 1/2006 | Smith et al. | |
| 7,218,971 B2 | 5/2007 | Heil, Jr. et al. | |
| 2002/0173521 A1 | 11/2002 | Smith et al. | |
| 2002/0198189 A1 | 12/2002 | Besencon et al. | |
| 2003/0125360 A1 | 7/2003 | Smith et al. | |
| 2003/0171368 A1 | 9/2003 | Seitz et al. | |
| 2003/0186967 A1 | 10/2003 | Kees et al. | |
| 2004/0039441 A1 | 2/2004 | Rowland et al. | |
| 2004/0063934 A1 | 4/2004 | Geneste et al. | |
| 2004/0077638 A1 | 4/2004 | Geneste et al. | |
| 2004/0077684 A1 | 4/2004 | De Corte et al. | |
| 2004/0086519 A1 | 5/2004 | Kumar et al. | |
| 2004/0106654 A1 | 6/2004 | Smith et al. | |
| 2004/0176838 A1 | 9/2004 | Mucha et al. | |
| 2004/0236108 A1 | 11/2004 | Smith et al. | |
| 2004/0241162 A1* | 12/2004 | Berenson et al. | 424/144.1 |
| 2004/0259923 A1 | 12/2004 | Inoue et al. | |
| 2005/0009835 A1 | 1/2005 | Thomas | |
| 2005/0026917 A1 | 2/2005 | Kinney | |
| 2005/0059669 A1 | 3/2005 | Ajito et al. | |
| 2005/0096360 A1 | 5/2005 | Salter-Cid et al. | |
| 2005/0187611 A1 | 8/2005 | Ding et al. | |
| 2005/0226873 A1 | 10/2005 | Del Priore et al. | |
| 2005/0267562 A1 | 12/2005 | Jones et al. | |
| 2006/0015146 A1 | 1/2006 | Girouard et al. | |
| 2006/0025438 A1 | 2/2006 | Salter-Cid et al. | |
| 2006/0030575 A1 | 2/2006 | Danthi et al. | |
| 2006/0041182 A1* | 2/2006 | Forbes et al. | 600/12 |

(Continued)

FOREIGN PATENT DOCUMENTS

WO WO-91/00360 A1 1/1991
WO WO-93/01221 A1 1/1993

(Continued)

OTHER PUBLICATIONS

DiVietro et al. (Journal of Immunology. 2001; 167:4017-4025).*
Cooke et al. (Parasitology Today. 1995; 11(8): 282-287).*
Hinds et al (J. Biomechanics. 2001; 34: 95-103).*
Tsuchiya et al. (Materials Science and Engineering. 2001; C17: 79-82).*
Wave Biotech presentation—2004.*
Greenberg et al. (Blood. 2000; 95: 478-486).*
Stroock et al. (Science. 2002; 295: 647-651).*
Brown et al. (Boundary-Layer Meteorology. 2001; 98: 411-441).*
Gradeck et al. (Experiments in Fluids. 1998; 24: 17-26).*
Lee Zhao (M.S. Thesis, Univeristy of Florida 2000).*
Blankenberg, Stefan , et al., "Adhesion molecules and atherosclerosis", *Atherosclerosis*, 170(2), (Oct. 2003),191-203.

(Continued)

*Primary Examiner* — Scott Long
(74) *Attorney, Agent, or Firm* — Schwegman Lundberg & Woessner, P.A.

(57) ABSTRACT

A device for altering the expression or activation of adhesion molecules on cells including endothelial cells, as well as methods for altering the expression or activation of adhesion molecules on cells including endothelial cells, are provided.

23 Claims, 7 Drawing Sheets

(56) References Cited

U.S. PATENT DOCUMENTS

| | | | |
|---|---|---|---|
| 2006/0085063 A1* | 4/2006 | Shastri et al. | 623/1.41 |
| 2006/0128770 A1 | 6/2006 | Inoue et al. | |
| 2006/0134071 A1 | 6/2006 | Ross et al. | |
| 2006/0264643 A1 | 11/2006 | Patel | |
| 2007/0003528 A1* | 1/2007 | Consigny et al. | 424/93.7 |
| 2008/0057053 A1 | 3/2008 | Stolen | |
| 2008/0058922 A1 | 3/2008 | Stolen | |

FOREIGN PATENT DOCUMENTS

| | | |
|---|---|---|
| WO | WO-98/30615 A1 | 7/1998 |
| WO | WO-98/58669 A2 | 12/1998 |
| WO | WO-03/091398 A2 | 11/2003 |

OTHER PUBLICATIONS

Christman, K. L., "Injectable Fibrin Scaffold Improves Cell Transplant Survival, Reduces Infarct Expansion, and Induces Neovasculature Formation in Ischemic Myocardium", *Journal of the American College of Cardiology*, 44(3), (Aug. 4, 2004),654-660.
Fujiyama, S., et al., "Bone marrow monocyte lineage cells adhere on injured endothelium in a monocyte chemoattractant protein-1-dependent manner and accelerate reendothelialization as endothelial progenitor cells", *Circulation Research*, 93(10), Nov. 14, 2003 ,980-9.
Gojo, S., "In vivo cardiovasculogenesis by direct injection of isolated adult mesenchymal stem cells", *Experimental Cell Research*, 288(1), (Aug. 1, 2003),51-59.
Houghton, Jeanmarie, et al., "Gastric Cancer Originating from Bone Marrow-Derived Cells", *Science*, 306(5701), (Nov. 26, 2004),1568-1571.
McGowan, N. W., et al., "Cytokine-activated endothelium recruits osteoclast precursors", *Endocrinology*, 142(4), (Apr. 2001),1678-81.
Menasche, P., "Cell transplantation in myocardium", *The Annals of Thoracic Surgery*, 75(6), (Jun. 2003),S20-S28.
Minami, E., "Skeletal muscle meets cardiac muscle. Friends or foes?", *J Am Coll Cardiol.*, 41(7), (Apr. 2, 2003),1084-6.
Petit, I., et al., "G-CSF induces stem cell mobilization by decreasing bone marrow SDF-1 and up-regulating CXCR4", *Nature Immunology*, 3(7), (Jul. 2002),687-94.
Sata, M., et al., "Inflammation, angiogenesis, and endothelial progenitor cells: how do endothelial progenitor cells find their place?", *Journal of Molecular and Cellular Cardiology*. 36(4), (Apr. 2004),459-463.
Tambara, K., "Transplanted Skeletal Myoblasts Can Fully Replace the Infarcted Myocardium When They Survive in the Host in Large Numbers", *Circulation*, 108 [*Suppl I*], (2003),II-259-II-263.
Vermeulen, M., et al., "Role of Adhesion Molecules in the Homing and Mobilization of Murine Hematopoietic Stem and Progenitor Ce", *Blood*, 92(3), (Aug. 1, 1998),894-900
Voermans, C., et al., "Adhesion molecules involved in transendothelial migration of human hematopoietic progenitor cells", *Stem Cells*, 18(6), (2000),435-43.
Zeiffer, U., et al., "Neointimal smooth muscle cells display a proinflammatory phenotype resulting in increased leukocyte recruitment mediated by P-selectin and chemokines", *Circulation Research*, 94(6), (Apr. 2, 2004),776-84.
Zhu, H., et al., "The Role of the Hyaluronan Receptor CD44 in MSC Migration in the Extracellular Matrix", *Stem Cells*, Epub ahead of print,(Nov. 23, 2005),1-32.
"Partial Prosecution File History for U.S. Appl. No. 11/469,081", (as of Jan. 10, 2008), 43 pgs.
Christman, K. L., "Injectable Fibrin Scaffold Improves Cell Transplant Survival, Reduces Infarct Expansion, and Induces Neovasculature Formation in Ischemic Myocardium", *Journal of the American College of Cardiology*, 44(3), (Aug. 4, 2004), 654-660.
Cohn, J. N., "Treatment of Infract Related Heart Failure: Vasodilators Other han ACE Inhibitors", *Cardiovascular Drugs and Therapy*;8, Kluwer Academic Publishers, Boston, (Dec. 1994), 119-122.

Dimmeler, S., et al., "Unchain My Heart: the Scientific Foundations of Cardiac Repair.", *J Clin Invest.*, 115(3), (Mar. 2005), 572-583.
Haider, H., et al., "Bone Marrow Stem Cell Transplantation for Cardiac Repair.", *Am J Physiol Heart Circ Physiol.*, 288(6), (Jun. 2005), H2557-H2567.
Hofmann, M., et al., "Monitoring of Bone Marrow Cell Homing Into the Infarcted Human Myocardium", *Circulation*, 111(17), (May 3, 2005), 2198-2202.
Losordo, D. W., et al., "Therapeutic Angiogenesis and Vasculogenesis for Ischemic Disease, Part II: Cell-Based Therapies", *Circulation*; 190, www.circulationaha.org,(Jun. 2004), 2 692-2697.
Lum, L. G., et al., "Targeting of Lin-Sca+ Hematopoietic Stem Cells With Bispecific Antibodies to Injured Myocardium", *Blood Cells Mol Dis.*, 32(1), (Jan.-Feb. 2004), 82-87.
Roth, C. M., et al., "Nucleic Acid Biotechnology", *Annual Review Biomedical Engineering*; 01, (1999), 265-297.
Schächinger, V., et al., "Transplantation of Progenitor Cells and Regeneration Enhancement in Acute Myocardial Infarction: Final One-Year Results of the TOPCARE-AMI Trial", *Journal of the American College of Cardiology*, 44(8), (Oct. 19, 2004), 1690-1699.
Wollert, K. C., et al., "Clinical Applications of Stem Cells for the Heart", *Circulation Research*, 96(2), (Feb. 4, 2005), 151-163.
Kreitman, R. J, "Recombinant toxins for the treatment of cancer.", *Curr Opin Mol Ther.*, 5(1), (Feb. 2003), 44-51.
"U.S. Appl. No. 11/469,081, Response filed Nov. 20, 2008 to Final Office Action mailed Aug. 21, 2008", 12 pgs.
"U.S. Appl. No. 11/469,081, Response filed Jan. 15, 2009 to Non Final Office Action mailed Dec. 16, 2008", 8 pgs.
"U.S. Appl. No. 11/469,081 Restriction Requirement mailed Apr. 27, 2009", 12 pgs.
"U.S. Appl. No. 11/469,081, Response filed May 27, 2009 to Restriction Requirement mailed Apr. 27, 2009", 11 pgs.
"U.S. Appl. No. 11/469,064, Non-Final Office Action mailed Feb. 20, 2009", 8 pgs.
"U.S. Appl. No. 11/469,064, Final Office Action mailed Jun. 9, 2009", 11 pgs.
"U.S. Appl. No. 11/469,064, Response filed May 29, 2009 to Non Final Office Action mailed Feb. 20, 2009", 12 pgs.
"U.S. Appl. No. 11/469,064, Response filed Oct. 21, 2009 to Final Office Action mailed Jun. 9, 2009", 17 pgs.
"U.S. Appl. No. 11/469,081, Non-Final Office Action mailed Aug. 4, 2009", 11 Pgs.
"U.S. Appl. No. 11/469,064, Non-Final Office Action mailed Jan. 12, 2010", 8 pgs.
"U.S. Appl. No. 11/469,081, Response filed Jul. 10, 2007 to Restriction Requirement mailed Jun. 11, 2007", 9 pgs.
"U.S. Appl. No. 11/469,081, Response filed Dec. 3, 2009 to Non Final Office Action mailed Aug. 4, 2009", 9 pgs.
"U.S. Appl. No. 11/469,081, Restriction Requirement mailed Jun. 11, 2007", 9 pgs.
"U.S. Appl. No. 11/469,064, Final Office Action mailed May 28, 2010", 11 pgs.
"U.S. Appl. No. 11/469,064, Response filed May 12, 2010 to Non Final Office Action mailed Jan. 12, 2010", 14 pgs.
"U.S. Appl. No. 11/469,064, Response filed Sep. 28, 2010 to Final Office Action mailed May 28, 2010", 15 pgs.
"U.S. Appl. No. 11/469,081, Response filed Jun. 22, 2010 to Final Office Action mailed Feb. 22, 2010", 10 pgs.
Bonanno, G., et al., "Human cord blood CD133+ cells immunoselected by a clinical-grade apparatus differentiate in vitro into endothelial-and cardiomyocyte-like cells", Transfusion, (Feb. 2000), 280-289.
Ceafalan, L., et al., "Expression of stem cell markers on fetal and tumoral human liver cells in primary culture", Rev Med Chir Soc Med Nat Iasi, (2005), 96-104.
Hsu, H, et al., "Hematopoietic stem cells express Tie-2 receptor in the murine fetal liver", Blood, (Dec. 2000), 3757-3762.
Jaatinen, T., et al., "Isolation of hematopoietic stem cells from human cord blood.", Curr Protoc Stem Cell Biol., Chapter 2, (Jun. 2007), Unit 2A.2.
Kerfoot, C., et al., "Cerebral cortical dysplasia: giant neurons show potential for increased excitation and axonal plasticity", Dev Neurosci, (Nov. 1999), 260-270.

(56) References Cited

OTHER PUBLICATIONS

Martinez, O. M., et al., "CD30 expression identifies a functional alloreactive human T-lymphocyte subset", Transplantation, (May 1998), 1240-1247.
Nathan, Carl, et al., "Cytokines in Context", Journal of Cell Biology vol. 113 No. 5, (Jun. 1991), 981-986.
Oh, J. D., et al., "Overexpression of neurotrophin receptor p75 contributes to the excitotoxin-induced cholinergic neuronal death in rat basal forebrain", Brain Res., (Jan. 2000), 174-185.
Salmi, Marko, et al., "Homing of Mucosal Leukocytes to Joints", J. Clin. Invest., (May 1997), 2165-2172.
Salmi, Marko, et al., "Human Vascular Adhesion Protein-1 (VAP-1) Plays a Critical Role in Lymphocyte-Endothelial Cell Adhesion Cascade Under Shear", Circ. Res 2000;86, (2000), 1245-1251.
Scherer, S. E., et al., "Expression and regulation of kainate and AMPA receptors in the rat neural tube", J. Neurosci Res, (May 1998), 356-368.
"U.S. Appl. No. 11/469,064, Non Final Office Action mailed Feb. 7, 2011", 18 pgs.
"U.S. Appl. No. 11/469,081, Non Final Office Action mailed Dec. 9, 2010", 15 pgs.
Arvilommi, A. M, et al., "Organ-selective regulation of vascular adhesion protein-1 expression in man", European Journal of Immunology, 27(7), (Jul. 1997), 1794-1800.
Frangogiannis, N. G., et al., "The Inflammatory Response in Myocardial Infarction", Cardiovascular Research, 53(1), (Jan. 2002), 31-47.
Granger, D. Neil, et al., "Recruitment of Inflammatory and Immune Cells in the Gut: Physiology and Pathophysiology", Physiology of the Gastrointestinal Tract, Fourth Edition, (2006), 1137-1162.
Hahne, Michael, et al., "Five Tumor Necrosis Factor-inducible Cell Adhesion mechanisms on the Surface of Mouse Endothelioma Cells Mediate the Binding of Leukocytes", The Journal of Cell Biology, vol. 121, No. 3, (May 1993), 655-664.
Janeway, Charles A, et al., "Chapter 10: Host Defense Against Infection", Immuno Biology: The Immune System in Health and Disease, Fourth Edition, (1999), 376-377.
Karupiah, Gunasegaran, "Cytokines and Chemokines in Infectious Diseases Handbook", Immunology and Cell Biology (2003) 81, (2003), 3 pgs, http:/www.nature.com/icb/journal/v81/n6/full/icb200371a.html, downloaded Apr. 28, 2011.
Lum, L. G, et al., "The new face of bispecific antibodies: targeting cancer and much more", Experimental Hematology, 34(1), (Jan. 2006), 1-6.
Mako, V, et al., "Proinflammatory activation pattern of human umbilical vein endothelial cells induced by IL-1β, TNF-a, and LPS", Cytometry A, 77(10), (Oct. 2010), 962-70.
Montgomery, Kevin F, et al., "Activation of endothelial-leukocyte molecule 1 (ELAM-1) gene transcription", Proc. Natl. Acad. Sci. USA, vol. 88, Medical Sciences, (Aug. 1991), 6523-6527.
Thompson, Angus W, "The Cytokine Handbook, Third Edition", (Jul. 1, 1998), 5 pgs http://www.amazon.com/Cytokine-Thompson.dp/0126896623, Downloaded Apr. 28, 2011.
"U.S. Appl. No. 11/469,064, Response filed Aug. 23, 2012 to Non Final Office Action mailed Mar. 29, 2012", 17 pgs.
"U.S. Appl. No. 11/469,064, Final Office Action mailed Sep. 5, 2012", 12 pgs.
"U.S. Appl. No. 11/469,064, Non Final Office Action mailed Mar. 29, 2012", 17 pgs.
"U.S. Appl. No. 11/469,081, Final Office Action mailed May 30, 2012", 11 pgs.
"U.S. Appl. No. 11/469,081, Response filed Aug. 22, 2012 to Final Office Action mailed May 30, 2012", 9 pgs.
Sherif, H. M. F., "In search of a new therapeutic target for the treatment of genetically triggered thoracic aortic aneurysms and cardiovascular conditions: insights from human and animal lathyrism", Interact Cardiovasc Thorac Surg., 11(3), (Sep. 2010), 271-276.
"U.S. Appl. No. 11/469,064, Final Office Action mailed Aug. 4, 2011", 20 pgs.
"U.S. Appl. No. 11/469,064, Response filed Jun. 7, 2011 to Non Final Office Action mailed Feb. 7, 2011", 21 pgs.
"U.S. Appl. No. 11/469,081, Final Office Action mailed Aug. 3, 2011", 10 pgs.
Carpene, C., "Chapter 12—Amine Oxidases in Adipose Tissue-Related Disorders", In: Copper Amine Oxidases: Structures, Catalytic Mechanisms and Role in Pathophysiology / Edition 1, CRC Press, (Jun. 2009), 177-194.
Hadri, K. E., et al., "Semicarbazide-Sensitive Amine Oxidase in Vascular Smooth Muscle Cells: Differentiation-Dependent Expression and Role in Glucose Uptake", Arteriosclerosis, Thrombosis and Vascular Biology, 22, (2002), 89-94.
Martelius, T., et al., "Inhibition of semicarbazide-sensitive amine oxidases decreases lymphocyte infiltration in the early phases of rat liver allograft rejection", Int J Immunopathol Pharmacol., 21(4), (Oct.-Dec. 2008), 911-920.
Marttila-Ichihara, F., et al., "Vascular Amine Oxidases Are Needed for Leukocyte Extravasation Into Inflamed Joints In Vivo", Arthritis & Rheumatism, 54(9), (Sep. 2006), 2852-2862.
O'Rourke, A. M, et al., "Benefit of inhibiting SSAO in relapsing experimental autoimmune encephalomyelitis", J Neural Transm., 114(6), (2007), 845-849.
Stolen, C. M, et al., "Absence of the Endothelial Oxidase AOC3 Leads to Abnormal Leukocyte Traffic In Vivo.", Immunity, 22(1), (Jan. 2005), 105-115.
Stolen, C. M, et al., "Origins of serum semicarbazide-sensitive amine oxidase", Circ Res., 95(1), (Jul. 9, 2004), 50-57.
Stolen, C. M, et al., "Semicarbazide sensitive amine oxidase overexpression has dual consequences: insulin mimicry and diabetes-like complications", FASEB J., 18(6), (Apr. 2004), 702-4.
Yraola, F., et al. "Structure-activity relationships of SSAO/VAP-1 arylalkylamine-based substrates", ChemMedChem., 4(4), (Apr. 2009), 495-503.
"U.S. Appl. No. 11/469,064, Response filed Dec. 5, 2011 to Final Office Action mailed Aug. 4, 2011", 18 pgs.
"U.S. Appl. No. 11/469,064, Final Office Action mailed Aug. 21, 2008", 6 pgs.
"U.S. Appl. No. 11/469,064, Non-Final Office Action mailed Jan. 24, 2008", 7 pgs.
"U.S. Appl. No. 11/469,064, Response filed Apr. 24, 2008 to Non-Final Office Action mailed Jan. 24, 2008", 11pgs.
"U.S. Appl. No. 11/469,081, Response filed Dec. 5, 2011 to Final Office Action mailed Aug. 3, 2011", 12 pgs.
"U.S. Appl. No. 11/469,081, Advisory Action mailed May 29, 2008", 8 pgs.
"U.S. Appl. No. 11/469,081, Final Office Action mailed Feb. 4, 2008", 10 pgs.
"U.S. Appl. No. 11/469,081, Non-Final Office Action mailed Aug. 22, 2007", 16 pgs.
"U.S. Appl. No. 11/469,081, Response filed May 1, 2008 to Final Office Action mailed Feb. 4, 2008", 11 pgs.
"U.S. Appl. No. 11/469,081, Response filed Sep. 9, 2008 to Non Final Office Action mailed Aug. 13, 2008", 8 pgs.
"U.S. Appl. No. 11/469,081, Response filed Nov. 21, 2007 to Non-Final Office Action mailed Aug. 22, 2007", 12 pgs.
"Oregovomab: anti-CA-125 monoclonal antibody 343.13—AltaRex, B43.13, MAb B43.13, monoclonal antibody B43.13", (Abstract), Drugs R D., 7(6), (2006), 2 pgs.
Aluigi. M., et al., "Nucleofection is an efficient nonviral transfection technique for human bone marrow-derived mesenchymal stem cells", Stem Cells, 24(2), (Feb. 2006), 454-61.
Arvilommi, A. M., et al., "Lymphocyte Binding to Vascular Endothelium in Inflamed Skin Revisited: A Central Role for Vascular Adhesion Protein-1 (VAP-1)", European Journal of Immunology, 26(4), (1996), 825-833.
Benita, S., et al., "Characterization of drug-loaded poly(d,l-lactide) microspheres", J Pharm Sci, 73(12), (Dec. 1984), 1721-1724.
Bertini, V., et al., "Alkylamino Derivatives of 4-Aminomethylpyridine as Inhibitors of Copper-Containing Amine Oxidases", J. Med. Chem., 48(3), (2005), 664-670.

(56) References Cited

OTHER PUBLICATIONS

Chen, X., et al., "Chemokines and chemokine receptors as novel therapeutic targets in rheumatoid arthritis (RA): inhibitory effects of traditional Chinese medicinal components", *Cell Mol Immunol.*, 1(5), (Oct. 2004), 336-342.
Chen, Y. F, et al., "A systematic review of the effectiveness of adalimumab, etanercept and infliximab for the treatment of rheumatoid arthritis in adults and an economic evaluation of their cost-effectiveness", (Abstract), *Health Technol Assess*, 10(42), (Nov. 2006), 2 pgs.
Chou, T. C., et al., "Quantitative analysis of dose-effect relationships: the combined effects of multiple drugs or enzyme inhibitors", *Advances in Enzyme Regulation* 22, (1984), 27-55.
Dostert, P., et al., "Inhibition of Semicarbazide-Sensitive Amine Oxidase by Monoamine Oxidase B Inhibitors From the Oxazolidinone Series", *Journal of Pharmacy and Pharmacology*, 36(11), (1984), 782-785.
Ellis, J., et al., "Engineered anti-CD38 monoclonal antibodies for immunotherapy of multiple myeloma", *The American Association of Immunologists*, 155(2), (1995), 925-937.
Goldmacher, V. S, et al., "Anti-CD38-blocked ricin: an immunotoxin for the treatment of multiple myeloma", *Blood*, 84(9), (Nov. 1, 1994), 3017-3025.
Gombotz, W. R., et al., "Protein Release from Alginate Matrices", *Advanced Drug Delivery* Reviews, 31(3), (1998), 267-285.
Gordon, E. J, et al., "Prolonged survival of rat islet and skin xenografts in mice treated with donor splenocytes and anti-CD154 monoclonal antibody", *Diabetes*, 47(8), (Aug. 1998), 1199-206
Gordon, E. J, et al., "Rat Xenograft Survival in Mice Treated with Donor-Specific Transfusion and Anti-CD154 Antibody is Enhanced by Elimination of Host CD4$^+$ Cells", *Transplantation*, 71(2) (Jan. 27, 2001), 319-327.
Greenlee, J. E, "Progressive multifocal leucoencephalopathy in the era of natalizumab: a review and discussion of the implications", (Abstract), *Int MS J.*, 13(3), (Nov. 2006), 1 pg.
Guo, Z., et al., "Blockade of CD4 Molecules by Nondepleting anti-CD4 Monoclonal Antiodies Prevents Xenogeneic Pig Islet Graft Rejecting and Recurrence of Autoimmune Diabetes.", *Transplantation*, vol. 67 (09), (May 15, 1999), 1 pg.
Guo, Z. G, et al., "Effect of Therapy with Non-Depleting Anti-CD4 Monoclonal Antibody and CTLA4Ig on Allogeneic Islet Graft Survival in Autoimmune Diabetic Nod Mice", (Abstract #659), *Transplantation*, vol. 69(8), (Apr. 27, 2000), p. S283.
Gupta, A. K, et al., "Efalizumab in the treatment of psoriasis", *J Cutan Med Surg.*, 10(2), (Mar.-Apr. 2006), Abstract.
Heller, J., et al., "Poly(ortho esters): Synthesis, Characterization, Properties and Uses", *Advanced Drug Delivery Reviews*, 54(7), (2002), 1015-1039.
Ho, V. T, et al., "The history and future of T-cell depletion as graft-versus-host disease prophylaxis for allogeneic hematopoietic stem cell transplantation", *Blood*. 98(12), (Dec. 1, 2001), 3192-3204.
Hou, W. C, et al., "Inhibitory activities of semicarbazide-sensitive amine oxidase and angiotensin converting enzyme of pectin hydroxamic acid", *J Agric Food Chem.*, 51(21), (Oct. 8, 2003), 6362-6366.
Hoy, S. M, et al., "Panitumumab: in the treatment of metastatic colorectal cancer", (Abstract), *Drugs*, 66(15), (2006), 1 pg.
Jones, H. A, "Inflammation imaging", *Proc Am Thorac Soc.*, 2(6), (2005), 545-8, 513-514.
Kirten, C. M., et al., "Function-Blocking Antibodies to Human Vascular Adhesion Protein-1: A Protein Anti-Inflammatory Therapy", *Eur. J. Immunol.*, 35, (2005), 3119-3130.
Kofler, S., et al., "Role of cytokines in cardiovascular diseases: a focus on endothelial responses to inflammation", (Abstract), *Clin Sci (Lond)*, 108(3), (Mar. 2005), 1 pg.
Koskinen, K., "Granulocyte Transmigration Through the Endothelium is Regulated by the Oxidase Activity of Vascular Adhesion Protein-1 (VAP 1)", Blood, 103(9), (2004), 3388-3395.
Lakshmipathy, U., et al., "Efficient transfection of embryonic and adult stem cells", Stem Cells, 22(4), (2004), 531-43.

Larsen, C. P., et al., "Long-term acceptance of skin and cardiac allografts after blocking CD40 and CD28 pathways.", Nature. 381(6581), (1996), 434-8.
Lazar, L., et al., "Synthesis of Hydrazing Alcohols With Anti-Inflammatory Activity", Acta Pharma. Hungarica, 74(1), (2004), 11-18.
Lehmann, M., et al., "Anti-CD4 Monoclonal Antibody-Induced Allograft Tolerance in Rats Despite Persistence of Donor-Reactive T Cells", Transplantation (Baltimore), 64(8), (Oct. 27, 1997), 1181-1187.
Lehnert, A. M, et al., "Pancreatic islet xenograft tolerance after short-term costimulation blockade is associated with increased CD4+ T cell apoptosis but not immune deviation", Transplantation, 69(6), (Mar. 27, 2000), 1176-85.
Lizcano, J. M, et al., "Amine Oxidase Activities in Chemically-Induced Mammary Cancer in the Rat", J Neural Transm Suppl., 32, (1990), 323-326.
Lu, X., et al., "Requirement of CD4 Cells for Induction and Maintenance of Unresponsiveness in Islet Xenografted Mice.", Xenotransplantation, 5(3), (Aug. 1998), 207-214.
Maguire, A. M, et al., "Allogeneic bone marrow transplant improves outcome for juvenile myelomonocytic leukaemia", J Paediatr Child Health, 38(2), (Apr. 2002), Abstract.
Mathiowitz, E., et al., "Morphology of polyanhydride microsphere delivery systems", Scanning Microscopy, 4(2), (Jun. 1990), 329-340.
Mathiowitz, E., "Novel Microcapsules for Delivery Systems", Reactive Polymers, Ion Exchangers, Sorbents, 6(2-3), (1987), 275-293.
Mathiowitz, E., et al., "Polyanhydride microspheres as drug carriers I. Hot-melt rnicroencapsulation", Journal of Controlled Release, 5(1), (Jun. 1987), 13-22.
Mathiowitz, E., et al., "Polyanhydride Microspheres as Drug Carriers. II. Microencapsulation by Solvent Removal", Journal of Applied Polymer Science, 35, (1988), 755-774.
Mathiowitz, E., et al., "Polyanhydride microspheres. IV. Morphology and characterization of systems made by spray drying", Journal of Applied Polymer Science, 45(1), (1992), 125-134.
Megeed, Z., et al., "Controlled Release of Plasmid DNA From a Genetically Engineered Silk-Elastinlike Hydrogel", Pharmaceutical Research, 19(7), (2002), 954-959.
Mizia-Stec, K., "Cytokines and adhesive molecules in detection of endothelial dysfunction", Pharmacological Reports, 58, (2006), 21-32.
Nash, G. B, et al., "The local physicochemical environment conditions the proinflammatory response of endothelial cells and thus modulates leukocyte recruitment.", (Abstract). *FEBS Lett.*, 569(1-3), (Jul. 2, 2004), 1 pg.
Obata, T., et al., "Evidence for Existence of Immobilization Stress-Inducible Semicarbazide-Sensitive Amine Oxidase Inhibitor in Rat Brain Cytosol", *Neuroscience Letters*, 296(1), (2000), 58-60.
O'Connor, P., "Natalizumab and the role of alpha 4-integrin antagonism in the treatment of multiple sclerosis", (Abstract), *Expert Opin in Biol Ther.*, 7(1), (Jan. 2007), 1 pg.
Piro, M., et al., "Endothelium and inflammation", (Abtract), *Panminerva Med.*, 47(2), (Jun. 2005), 1 pg.
Riederer, P., et al., "Clinical applications of MAO-inhibitors", (Abstract), *Curr Med Chem.*, 11(15), (Aug. 2004), 1 pg.
Roy, K., et al., "Gene Delivery with In-situ Crosslinking Polymer Networks Generates Long-Term Systemic Protein Expression", *Molecular Therapy*, 7, (2003), 401-408.
Salmi, M., et al., "Induction and Function of Vascular Adhesion Protein-1 at Sites of Inflammation", *Journal of Experimental Medicine*, 178(6), (1993), 2255-2260.
Stolen, C. M, et al., "Semicarbazide-sensitive amine oxidase overexpression has dual consequences: insulin mimicry and diabetes-like complications", *FASEB J.*, 18(6), (Apr. 2004), 702-4.
Tousoulis, D., et al., "Endothelial function and inflammation in coronary artery disease.", *Heart*, 92(4), (Apr. 2006), 441-4.
Wang, E. Y, et al., "Design, synthesis, and biological evaluation of semicarbazide-sensitive amine oxidase (SSAO) inhibitors with anti-inflammatory activity.", J. Med. Chem., 49(7), (Apr. 6, 2006), 2166-2173.
Wognum, A. W, et al., "Identification and isolation of hematopoietic stem cells", *Arch Med Res.*, 34(6), (Nov.-Dec. 2003), 461-475.

(56) References Cited

OTHER PUBLICATIONS

Wu, T., et al., "Cardiovascular disease in diabetic nephropathy patients: cell adhesion molecules as potential markers?", *Vasc Health Risk Manag*,. 1(4), (2005), 309-16.

Yegutkin, G. G., et al., "A Peptide Inhibitor of Vascular Adhesion Protein-1 (VAP-1) Blocks Leukocyte-Endothelium Interactions Under Shear Stress", *European Journal of Immunology*, 34(8), (2004), 2276-2285.

* cited by examiner

METHODS AND DEVICES TO REGULATE STEM CELL HOMING

FIELD OF THE INVENTION

This invention relates generally to therapy of living tissue which employs, but not by way of limitation, the use of an agent that enhances or inhibits expression or activation of one or more adhesion molecules, and systems and devices therefor.

BACKGROUND

Stem/progenitor cell transplantation has emerged as a potential therapeutic modality for numerous conditions. For cardiac applications, cell injections have usually been accomplished under direct control through multiple epicardial punctures. However, to reduce the invasiveness of the procedure, percutaneous approaches are undergoing development. In the setting of these percutaneous techniques, the transvenous approach, using a specifically dedicated coronary sinus catheter, is particularly attractive because of its greater simplicity compared with the endoventricular route. Initial studies have established the effectiveness of bone marrow stem cell (BMC) transvenous transfer into the myocardium (Thomson et al., *J. Am. Coll. Cardiol.*, 34:7514 (2002)). Intracoronary injections of bone marrow mononuclear cells concomitant with angioplasty at the acute stage of myocardial infarction (MI) have also shown promising results (Strauer et al., *Circ.*, 106:1913 (2002); Assmus et al., *Circ.*, 106:3009 (2002)).

More recent efficacy data from preliminary studies in which patients with an acute MI were treated by application of BMC showed a 7-9% improvement in global LV ejection fraction, as well as improvements in regional wall motion, perfusion, and LV end systolic volumes four to six months after intracoronary BMC transplantation (see Wollert et al., *Circ. Res.* 96:151 (2005); Haider et al., *Am. J. Physiol. Circ. Physiol.*, 288:H2557 (2005); Dimmeler et al., *J. Clin. Investig.*, 115:572 (2005)). In particular, the final one-year results of the TOPCARE-AMI trial, demonstrated a sustained improvement of LV function, reduced infarct size, and an absence of reactive hypertrophy after intracoronary BMC transplantation, suggesting functional regeneration of the infarcted ventricles and a prevention of remodeling (Schachinger et al., *J. Am. Coll. Cardiol.*, 44:1690 (2004)). These findings are despite the observation that only 1.3-2.6% of the transplanted BMC are ultimately retained in the infarct after intracoronary transfer (Hofmann et al., *Circ.*, 111:2198 (2005)).

However, most transplanted cells never initially engraft (Christman et al., *J. Am. Coll. Cardiol.* 44:465 (2004)), very few are viable within one week post injection (Gojo et al., *Exp. Cell. Res.*, 288:51 (2003)), and the vast majority of transplanted cells die (Minami et al., *J. Am. Coll. Cardiol.*, 41:1084 (2003)). Thus, regardless of the route of delivery, cell number and cell death remain major limitations of cell transplantation. For instance, it is uncertain whether multiplication of those that have survived can replace the high attrition rate.

What is needed is an improved method to enhance homing, engraftment and retention of transplanted therapeutic cells.

SUMMARY OF THE INVENTION

Cell therapy has the potential to treat many pathological conditions, although a major problem with cell treatment modalities is poor stem cell homing, engraftment and retention at the site of interest. The invention provides methods and compositions for enhancing (increasing) targeting of donor cells, e.g., stem cells, to a specific site and optionally increasing their retention at that site, by providing for donor cells to establish additional contacts, firmly adhere, extravasate, and/or interact with the target tissue, cell or site, for instance, in a paracrine manner (e.g., by releasing a soluble therapeutic factor). Donor cells, endogenous cells or tissue at the site of interest, or both, are treated so as to enhance expression or activation of adhesion molecules. When the donor cells come into contact with the tissue in need of repair or site of interest, the donor cells adhere, e.g., reversibly adhere, to the tissue or site as a result of increased expression or activation of adhesion molecules, repopulate the tissue or site, provide paracrine factors and optionally differentiate into functional cells due to influences of the environment. The invention is thus widely applicable to any condition amenable to cell therapy, e.g., treatment of heart disease, e.g., MI, heart failure and cardiomyopathies, diabetes, Alzheimer's disease, spinal cord damage, arthritis, etc.

In one embodiment, the invention provides a system including a device, e.g., one adapted to deliver donor cells, and a population of donor cells having increased expression or activation of one or more adhesion molecules, e.g., as a result of contact with the device which may be coated or embedded with, or both, an agent that increases expression or activation of adhesion molecules on the donor cells, or as a result of contact with the agent in vitro. For example, the inside lumen of a catheter may be lined with one or more agents, e.g., a peptide, that activate adhesion molecules, on cells that are useful for cell therapy. Thus, adhesion molecules on donor cells in the lumen of a catheter are activated by their interaction with the agents lining the lumen of the catheter, e.g., during delivery of the cells. In one embodiment, the one or more agents are linked to the device, e.g., using a linker such as a polyethylene glycol (PEG) based linker. In one embodiment, the agent coated on or embedded in the device is not an antibody. In another embodiment, donor cells are contacted ex vivo with a device with a surface modified to activate or enhance expression of adhesion molecules.

In another embodiment, the invention provides a method to enhance donor cell homing in a mammal subjected to cell therapy. The method includes delivering to a mammal in need of cell therapy donor cells and an effective amount of a composition comprising an agent that increases the amount or activation of endogenous adhesion molecules on endothelial cells in the mammal. The present invention thus provides for increased homing and retention of transplanted donor cells by manipulating the expression of adhesion molecules on endogenous tissue, e.g., endothelial cells. The increased expression allows for increased homing of donor cells to particular sites, for instance, sites of inflammation, thus increasing the efficacy of cell therapy. For instance, the agent may be a cytokine, e.g., IL-8, IL-6 or TNF-α, or other molecule, e.g., lipopolysaccharide (LPS) or dimethylsulfoxide (DMSO), or a combination thereof. In one embodiment, the agent is not an antibody.

In another embodiment, endogenous tissue is treated, e.g., to hypoxic conditions, altered pH, altered temperature, pacing, or a combination thereof, thereby resulting in an increase in the amount or activation of endogenous adhesion molecules on endothelial cells in the mammal. In one embodiment, endogenous tissue is preconditioned with an agent that induces expression of vascular adhesion protein-1 (VAP-1) or other molecules related to adhesion and/or inflammation such as E-selectin, intercellular adhesion molecule (ICAM), glycoprotein IIB, IL-2, IL-4, IL-1b, TGF-beta, and the like. In one embodiment, expression of platelet activating factor (PAF), P selectin, VAP-1, one or more cytokines, ICAM-1, or a combination thereof, in endogenous cells, is increased. In one embodiment, to increase bone marrow cell (BMC) homing and engraftment to old infarcts, endogenous tissue may be activated by ischemia, pacing, irritants, e.g., LPS, TNF-α, cytokines or vagal nerve stimulation.

In one embodiment, the present invention provides for increased homing and retention of transplanted cells by manipulating the expression of adhesion molecules on donor cells, e.g., donor stem cells, or donor cells and endogenous tissue, e.g., endothelial cells, to allow for increased homing of donor cells to particular sites, for instance, sites of inflammation, thus increasing the efficacy of cell therapy. In order for cells to extravasate from the circulation and home to a specific site, they must make contact with the vessel wall, break their motion and firmly adhere.

Further provided is a method to enhance activated integrin expression on donor cells ex vivo. The method includes contacting donor cells and an effective amount of composition comprising an agent that increases expression or activation of integrin. In one embodiment, the agent comprises a transgene that encodes a gene product that enhances the expression of adhesion molecules on the donor cells, e.g., the expression of LFA-1 or Mac-1. In one embodiment, to deliver the cells and/or the agent, a catheter is employed. For instance, a catheter is employed to deliver the agent or a treatment that activates or increases expression of adhesion molecules, and donor cells which optionally have increased expression or activation of adhesion molecules.

In one embodiment, the donor cell is a stem cell having an antigen including but not limited to CD34, CD133, ABCG2, Sca-1, Stro-1, Nestin, PSA-NCam, p75 neurotrophin, c-kit, CD30, and the like. In one embodiment, the agent includes but is not limited to an agent that modulates inflammatory markers or adhesion molecules, e.g., VAP-1, P-selectin, E-selectin, ICAM, vascular cellular adhesion molecule (VCAM), vascular leukocyte adhesion (VLA), etc., and soluble forms thereof. The agent may be contacted with an endogenous tissue or cells, such as cardiac tissue, pancreatic tissue, neuronal cells, microglial cells, and synovial fluid secreting cells, donor cells, or both. In one embodiment, the methods of the invention are used for the repopulation of destroyed cells, for instance, in an organ in need of repair, for example, kidneys, liver, heart, lungs, intestines and the like, which may be highly advantageous in patients suffering from spinal cord trauma, diabetes, organ damage, or Alzheimer's disease.

In another embodiment, agents that inhibit or block binding of endogenous circulating cells, e.g., stem cells, are employed to decrease endogenous cell implantation at a selected site. For example, VAP-1 inhibitors, e.g., semicarbazide sensitive amine oxidase (SSAO) inhibitors, may be employed. The delivery of VAP-1 inhibitors, e.g., via a stent, in an effective amount may inhibit inflammation, restenosis, oxidative stress, e.g., reactive oxygen species (ROS) production, or a combination thereof. In one embodiment, the VAP-1 inhibitor may be an antibody, e.g., a humanized, chimeric, or ScFv antibody. In another embodiment, the VAP-1 inhibitor is not an antibody, for instance, the VAP-1 inhibitor is a drug containing a hydrazine, arylalkylamine, propenylamine, proparylamine, oxazolidinone or haloalkylamine. In one embodiment, one or more VAP-1 inhibitors are combined with a carrier such as a polymer, phosphorylcholine, or a ceramic, to provide for sustained release of the one or more inhibitors. In one embodiment, the one or more VAP-1 inhibitors are administered along with an immunosuppressive and/or an antiproliferative, for instance, sirolimus (rapamycin), paclitaxel, zotarolimus or everolimus. The immunosuppressive or antiproliferative may be administered separately or via the same delivery vehicle as the VAP-1 inhibitor, e.g., via the same stent or lead, to the same mammal.

In one embodiment, diabetics are at increased risk for restenosis after coronary angioplasty stenting. For example, diabetics having increased VAP-1 levels may particularly benefit from placement of a stent having one or more VAP-1 inhibitors. Also provided is a method of using VAP-1 inhibitor.

In one embodiment, donor cells are locally administered. In another embodiment, donor cells are systemically administered. Agents that enhance expression or activation, or inhibit or block, adhesion molecules may be locally administered or systemically administered, but preferably are locally delivered to or near a physiologic site. For instance, agents that enhance or activate adhesion molecules may be locally delivered, to or near a physiologic site which may benefit from cell therapy, e.g., damaged regions of the heart, pancreas, kidney, liver, spinal cord, brain and the like.

The invention includes compositions having one or more agents that enhance expression of adhesion molecules on donor cells and/or endogenous tissue or cells, and devices useful to deliver donor cells and/or agents.

DETAILED DESCRIPTION OF THE INVENTION

Definitions

Figure 1:
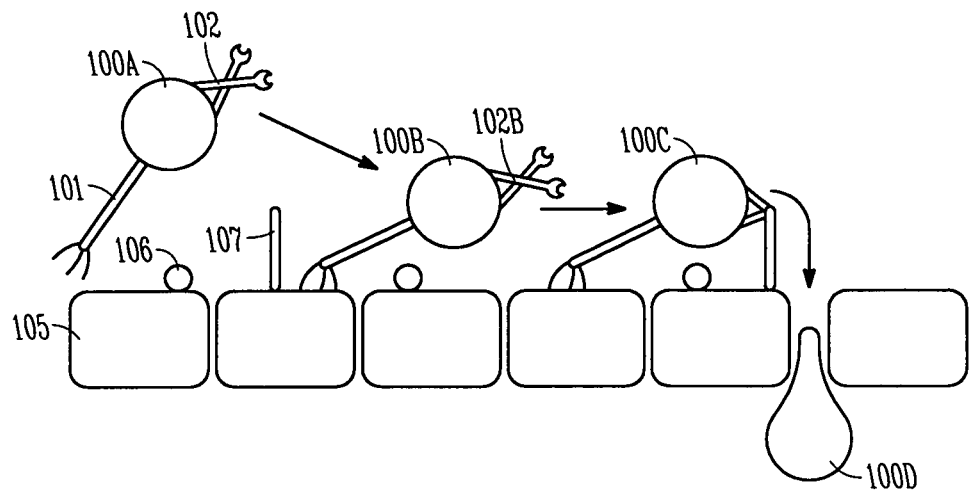
FIG. 1 is an illustration of cell homing.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene"), e.g., via a recombinant virus, into a host cell or by a genetically modified donor cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the cell if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" or "genetically modified cell" is meant a cell containing a transgene. For example, a stem cell transformed with a vector containing an expression cassette can be used to produce a population of cells having altered phenotypic characteristics.

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation stimulations are located 3' or downstream of the coding region.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation stimulations, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a stimulation or targeting peptide sequence is operably linked to another protein if the resulting fusion is secreted from a cell as a result of the presence of a secretory stimulation peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination stimulation, may also be included.

The term "exogenous," when used in relation to a protein, gene or nucleic acid, e.g., polynucleotide, in a cell or organism refers to a protein, gene, or nucleic acid which has been introduced into the cell or organism by artificial or natural means, or in relation to a cell refers to a cell which was isolated and subsequently introduced to other cells or to an organism by artificial or natural means (a "donor" cell). An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and "protein" are used interchangeably herein unless otherwise distinguished to refer to polymers of amino acids of any length. These terms also include proteins that are post-translationally modified through reactions that include glycosylation, acetylation and phosphorylation.

"Stem cells" are pluripotent or multipotent cells that can differentiate into multiple cell types. Stem cells also include cells that can transdifferentiate into at least one other cell type. A "precursor cell" or "progenitor cell" can be any cell in a specific differentiation pathway that is capable of differentiating into a more mature cell. A "differentiated cell" is a cell which is not capable of differentiating into a more mature cell under normal physiological conditions. As such, the term "precursor cell population" refers to a group of cells capable of developing into a more mature cell. A precursor cell population can comprise cells that are totipotent, cells that are pluripotent and cells that are stem cell lineage restricted (i.e., cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

Stem cells or precursor cells include but are not limited to, e.g., peripheral blood stem cells (PBSC), stem cells isolated from bone marrow (bone marrow cells; BMCs); stem cells isolated from adipose tissue; mesenchymal stem cells (MSCs), stem cells isolated from umbilical cord blood, menstral fluid, cardiac derived cells, embryonic stem cells, $CD30^+$ cells, $CD34^+$ cells, $CD34^-$ cells, $CD9^+$cells, $CD29^+$ cells, $CD44^+$ cells, $CD45^+$ cells, $CD49^+$ cells, $CD54^+$ cells, $CD56^+$ cells, $CD59^+$ cells, $CD71^+$ cells, $CD90^+$ cells, e.g., $CD90.1^+$ or $CD90.2^+$ cells, $CD105^+$ cells, $CD133^+$ cells, $CD135^+$ (flt-$3^+$) cells, $CD140a^+$ cells, $CDCP1^+$ cells, $CD146^+$ (muc-$18^+$) cells, $ABCG2^+$ cells, $CD144^+$ cells, fetal liver kinase $1^+$ cells, Stro-$1^+$ cells, $CD117^+$ (c-kit$^+$) cells, nestin$^+$ cells, PSA-NCAm$^+$ cells, $CD30^+$ cells, p75neurotophin$^+$ cells, $CD106^+$ cells, $CD120a^+$ cells, $CD124^+$ cells, $CD166^+$ cells, stem cell factor+ (SCF+) cells, Sca-$1^+$ cells, $SH2^+$ cells, $SH3^+$ cells, HLA, e.g., HLA-ABC cells, bone morphogenic protein protein+ (BMP) cells, e.g., $BMP2^+$ and $BMP4^+$ cells, $Gap43^+$ cells, glial fibrillary acidic protein$^+$ ($GFAP^+$) cells, myelin basic protein$^+$ ($MBP^+$) cells, $O4^+$ cells, $O1^+$ cells, synaptophysin$^+$ cells, alkaline phosphatase$^+$ cells, cripto$^+$ ($TDGF-1^+$) cells, podocalyxin$^+$ cells, sulfated proteoglycan$^+$ cells, e.g., silylated keratin sulfate proteoglycan$^+$ cells, stage-specific embryonic antigen$^+$ (e.g., SSEA-1, -3 and -4) cells, TRA-1-$60^+$ cells, TRA-1-$81^+$ cells, osteocalcin$^+$ cells, matrix gla protein$^+$ cells, osteopontin$^+$ cells, $Thy1^+$ cells, collagen type $II^+$ cells, collagen type $IV^+$ cells, fatty acid transporter$^+$ cells, and β-1 integrin$^+$ cells.

The term "stem cell specific antigen" or "precursor cell specific antigen" includes a protein, carbohydrate, or glycoprotein present on the surface of a stem or precursor cell. Antigens expressed on the surface of a stem cell include antigens expressed solely on the surface of a stem cell as well as antigens expressed on other cells. Different types of stem cells express different cell surface markers and therefore cells can be identified by the presence of a cell surface marker.

As used herein, "adhesion molecules" include but are not limited to selecting, e.g., L-selectin, E-selectin and P-selectin, mucines, integrins, e.g., LFA-1 and ICAM-1, Ig superfamily members, VAP-1, ectoenzymes, and ligands thereof. For instance, VLA-4 (an integrin) binds VCAM (CD106), LFA-1 (an integrin, CD11/18) binds ICAM (CD54), L-selectin (CD62) binds CD34, and CD44 binds hyaluronan (HA).

As used herein, the term "population" refers to cells having the same or different identifying characteristics. The term "lineage" refers to all of the stages of the development of a cell type, from the earliest precursor cell to a completely mature cell (i.e., a specialized cell).

The terms "effective amount" or "amount effective to" or "therapeutically effective amount" refers to an amount sufficient to induce a detectable therapeutic response in the subject. Assays for determining therapeutic responses are well known in the art. For example repair (i.e., healing) of injured myocardium can be detected using magnetic resonance imaging (MRI) to detect changes in the myocardium that are indicative of tissue regrowth and reformation.

The terms, "patient", "subject" or "animal" are used interchangeably and refer to a mammalian subject to be treated, with human patients being preferred In some cases, the methods of the invention find use in experimental animals, in veterinary application, and in the development of animal models for disease, including, but not limited to, rodents including mice, rats, and hamsters; and primates.

As used herein, "administering" or "delivering" a molecule to a cell (e.g., a molecule such as an expression vector, a delivery vehicle, an agent that enhances expression of tissue, cell or condition specific antigens, or an agent that enhances expression of adhesion molecules, and the like) includes contacting the molecule with the cell, e.g., by mixing without agitation or with agitation such as unidirectional flow ("rolling"), fusing, transducing, transfecting, microinjecting, electroporating, or via physical force ("shooting").

A "drug" as used herein is not a molecule encoded by or produced by a vertebrate cell or a vertebrate, but is one which in an effective amount has a therapeutic or prophylactic effect.

General Overview

This document describes, among other things compositions, methods and devices to enhance cell therapy. In one embodiment, in order to increase the accuracy and efficiency of donor cell homing, an agent that enhances expression or activation of adhesion molecules may be employed. The agent may be contacted with donor cells prior to or during cell administration (delivery), or may be separately administered to a physiological site of interest. The agent to enhance expression or activation of adhesion molecules may be administered systemically or locally (e.g., via injection, stent or catheter delivery). The administration of the agent to donor cells or endogenous tissue may allow the donor cells to establish additional contacts, firmly adhere, extravasate, and/or interact with the target tissue, cell or site, for instance, in a paracrine manner (e.g., by releasing a soluble therapeutic factor including a recombinant soluble factor).

In another embodiment, the invention provides for increased homing and retention of transplanted donor cells by manipulating the expression of adhesion molecules on the donor cells, e.g., donor stem cells, and/or endogenous tissue, e.g., endothelial cells. The increased expression allows for increased homing of donor cells to particular sites, for instance, sites of inflammation, thus increasing the efficacy of cell therapy. For example, the methods include the use of stem or other donor cells for the treatment of heart disease, such as myocardial infarction, heart failure, and cardiomyopathy, diabetes, Alzheimer's disease, spinal cord damage, arthritis, as well as other conditions. In order for cells to extravasate from the circulation and home to a specific site, they must make contact with the vessel wall, break their motion and firmly adhere. For example, an administered donor cell encounters an injured area having activated endothelium, which has increased expression of adhesion molecules such as platelet activating factor (PAF), P-selectin, and/or VAP-1, as well as optionally increased expression of cytokines, resulting in reversible binding between the donor cell and the activated endothelium. Interaction between the donor cell and activated endothelium causes activation of integrins on the donor cells, e.g., LFA-1 or Mac-1, and interaction between activated integrins and ICAM on the endothelium provides for tight binding of donor cells to the endothelium.

Further provided is the use of agents that enhance expression of adhesion molecules on donor cells and/or endogenous tissue or cells, and devices useful to deliver donor cells, agents, or a combination thereof. In one embodiment, the invention provides a composition including donor cells and an agent that enhances expression or activation of adhesion molecules. Agents useful in the methods of the invention include those which enhance cell surface molecule expression on target tissue or cells.

In one embodiment, to enhance donor cell capture and extravasation after donor cell delivery into the circulation, donor cells are treated ex vivo to increase expression or activation of adhesion molecules (e.g., activated integrins). For instance, donor cells are exposed ex vivo to an activated endothelial cell surface or other surface coated with activating agents (for example, a desirable surface structure, receptors, chemokines, antibodies, peptides, and the like). In another embodiment, donor cells are treated ex vivo with one or more soluble factors such as small molecules including a peptide, e.g., chemokines, soluble receptors, or antibodies that increase adhesion molecule expression or activation. In one embodiment, donor cells are contacted with agonistic antibodies immobilized on a solid surface. In another embodiment, donor cells are contacted with soluble molecules, e.g., soluble adhesion molecules found on activated endothelium. In yet another embodiment, donor cells are modified with a gene, e.g., by transfection with a plasmid encoding an adhesion molecule or an activator thereof, yielding genetically modified donor cells. In another embodiment, donor cells are subjected to ischemic conditions, pacing, irritants, e.g., molecular components of microorganisms not found in multicellular higher eukaryotes, including but not limited to molecular components of bacterial cells such as peptidoglycans, teichoic acids, lipopolysaccharide (LPS), mannans, flagellin, pilin, and bacteria DNA, and pattern recognition molecules for viral double stranded RNA and fungal cell wall components, e.g., lipoteichoic acids, glycolipids, mannans, and zymosan, TNF-α or one or more cytokines, so as to increase expression or activation of adhesion molecules. In one embodiment, delivery catheter lumens may be coated with an agent that increases expression or activation of adhesion molecules, for instance, lined with activated endothelium, e.g., irradiated or chemically fixed endothelium, cultured endothelium activated with TNF-α or IL-1, cultured endothelium that secretes one or more cytokines (e.g., IL-8), or cultured genetically modified endothelium, in order to activate the donor cells at the time of their administration (delivery).

In another embodiment, in order to enhance (increase) donor cell homing and extravasation, the target tissue for homing is exposed to an agent that enhances appropriate adhesion molecule expression on endogenous endothelial cell surfaces. For example, cytokines (e.g., TNF-α, IL-6, IFNγ or IL-8) or other agents, such as LPS, may be applied locally before or during the delivery of donor cells to enhance appropriate adhesion molecule expression on endogenous endothelial cell surfaces. In one embodiment, to increase bone marrow cell homing and engraftment to old infarcts, endogenous tissue may be activated by ischemic conditions, pacing, irritants, e.g., LPS, TNF-α, cytokines or vagal nerve stimulation. In one embodiment, a delivery vehicle, e.g., a particle such as a bead, for instance, a biodegradable bead, coated with adhesion molecules is administered to a target tissue. In another embodiment, a particle that elutes cytokines is administered to a target tissue, e.g., endothelial tissue via a catheter. In one embodiment, the agent or agent containing particles are delivered by a catheter (e.g., via the coronary arteries post myocardial infarction or for angina). In another embodiment, donor cell delivery catheters may be coated with adhesion molecules or lined with activated endothelium in order to activate adhesion molecules, such as integrins, on the donor cells prior to and/or during donor cell administration.

The invention also provides methods to inhibit homing and/or extravasation of endogenous cells by administering an agent that blocks or inhibits binding of the adhesion molecules to a target tissue. For example, small molecule inhibitors or antibodies to adhesion molecules such as antibodies to VAP-1, selecting, or integrins, may be applied to a tissue, e.g., locally, to prevent or inhibit unwanted endogenous stem cell homing. In one embodiment, an agent that blocks or inhibits adhesion molecules may be incorporated into a stent to prevent or reduce restenosis, e.g., to block or inhibit smooth muscle cells derived from circulating stem cells. For instance, a sustained release form of one or more VAP-1 inhibitors is applied to or incorporated in a stent, e.g., a metal or biodegradable stent, in an amount effective to prevent or reduce restenosis. In another embodiment, an adhesion inhibiting agent may be injected into a tumor (e.g., to prevent or inhibit angiogenesis). In yet another embodiment, an adhesion inhibiting agent may be injected into a heart (e.g., to prevent or inhibit cardiomyopathy or scarring). Thus, the invention may be useful to inhibit or treat many conditions including but not limited to myocardial infarction, heart failure, cardiomyopathy, restenosis, cancer and other diseases.

Potential Donor Cells and Exemplary Isolation Thereof

A cell population useful in the present invention is one which is capable of developing into cells of mesodermal cell lineage, ectodermal cell lineage and/or endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. In one embodiment, cells within a stem cell population for use in the present invention include cells of at least one of the following cellular lineages: hematopoietic cell lineage, endothelial cell lineage, epithelial cell lineage, muscle cell lineage and/or neural cell lineage or having the potential to differentiate into one or more of these lineages.

A variety of stem and progenitor cell populations may be used for repair of tissue. Each cell type has its own profile of advantages. For instance, unfractionated bone marrow cells (BMCs) contain different stem and progenitor cell populations, including HSCs, endothelial progenitor cells (EPCs), and mesenchymal stem cells (MSCs). Ease of harvest and lack of extensive requirement for ex vivo manipulation are advantages of using unselected BMCs.

EPCs were originally defined by their cell surface expression of the hematopoietic marker proteins CD133 and CD34 and the endothelial marker vascular endothelial growth factor receptor-2, and their capacity to incorporate into sites of neovascularization and to differentiate into endothelial cells in situ (Asahara, *Am. J. Physiol. Cell Physiol.*, 287:C572 (2004)). Increasing evidence suggests that culture-expanded EPCs also contain a CD14$^+$/CD34$^-$-mononuclear cell population with "EPC capacity," which mediates its angiogenic effects by releasing paracrine factors (Rehman et al., *Circulation* 107:1165 (2003); Urbich et al., *Circ. Res.,* 95:343 (2004)).

The cell surface antigen CD133 is expressed on early HSCs and EPCs, both of which collaborate to promote vascularization of ischemic tissues (Rafii et al., *Nat. Med.,* 9:702 (2003)). CD133$^+$ cells can integrate into sites of neovascularization and differentiate into mature endothelial cells. Because CD133 expression is lost on myelomonocytic cells, this marker provides an effective means to distinguish "true" CD133$^+$ EPCs from EPCs of myelomonocytic origin (Rehman et al., supra). Less than 1% of nucleated BMCs are CD133$^+$, and because these cells cannot be expanded ex vivo, only limited numbers of CD133$^+$ cells can be obtained for therapeutic purposes.

MSCs represent a rare population of CD34$^-$ and CD133$^-$ cells present in bone marrow stroma (10-fold less abundant than HSCs) and other mesenchymal tissues (Pittenger et al.,

*Circ. Res.,* 95:9 (2004)). MSCs can readily differentiate into osteocytes, chondrocytes, and adipocytes. Differentiation of MSCs to cardiomyocyte-like cells has been observed under specific culture conditions and after injection into healthy or infarcted myocardium in animals (Makino et al., *J. Clin. Invest.,* 103:697 (1999); Toma et al., *Circulation,* 105:93 (2002); Mangi et al., *Nat. Med.,* 9:1195 (2003)). When injected into infarct tissue, MSCs may enhance regional wall motion and prevent remodeling of the remote, noninfarcted myocardium (Mangi et al., 2003; Shake et al., *Ann. Thorac. Surg.,* 73:1919 (2002). Cultured MSCs secrete angiogenic cytokines, which improve collateral blood flow recovery in a murine hind limb ischemia model (Kinnaird et al., *Circ. Res.,* 94:678 (2004)). Because MSC clones can be expanded in vitro, and reportedly have a low immunogenicity, they may be used in an allogeneic setting (Pittenger et al., *Circ. Res.,* 95:9 (2004)).

Skeletal myoblasts, or satellite cells, are progenitor cells that normally lie in a quiescent state under the basal membrane of mature muscular fibers. Myoblasts can be isolated from skeletal muscle biopsies and expanded in vitro. Myoblasts differentiate into myotubes and retain skeletal muscle properties when transplanted into an infarct scar (Ghostine et al., *Circulation,* 106:I131 (2002); Murry et al., *J. Clin. Invest.,* 98:2512 (1996); Leobon et al., *Proc. Natl. Acad. Sci. USA,* 100:7808 (2003); Pagani et al., *J. Am. Coll. Cardiol.,* 41:879 (2003)). Myoblast transplantation has been shown to augment systolic and diastolic performance in animal models of myocardial infarction (Dowell et al., *Cardiovasc. Res.,* 58:336 (2003)).

Resident cardiac stem cell (CSC) population(s) are capable of differentiating into cardiomyocyte or vascular lineages (Hierlihy et al., *FEBS Lett.,* 530:239 (2002); Beltrami et al., *Cell,* 114:763 (2003); Oh et al., *Proc. Natl. Acad. Sci. USA,* 100:12313 (2003); Martin et al., *Dev. Biol.,* 265:262 (2004); Messina et al., *Circ. Res.,* 95:911 (2004)). Intriguingly, CSCs can be clonally expand from human myocardial biopsies (Messina et al., 2004). It has been reported that intramyocardial injection of these cells after AMI in mice promotes cardiomyocyte and vascular cell formation and leads to an improvement in systolic function (Messina et al., 2004).

Embryonic stem (ES) cells are totipotent stem cells derived from the inner cell mass of blastocysts. Under specific culture conditions, ES cells differentiate into multicellular embryoid bodies containing differentiated cells from all three germ layers including cardiomyocytes. Human ES cell-derived cardiomyocytes display structural and functional properties of early-stage cardiomyocytes that couple electrically with host cardiomyocytes when transplanted into normal myocardium (Kehat et al., *J. Clin. Invest.,* 108:407 (2001); Kehat et al., *Nat. Biotechnol.,* 22:1282 (2004)). Nuclear transfer techniques provide a means for generating an unlimited supply of histocompatible ES cells for the treatment of cardiac disease (therapeutic cloning) (Lanza et al., *Circ. Res.,* 94:820 (2004)).

Donor cells within the scope of the invention include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated $CD34^+$ cells, multipotent adult progenitor cells, adult stem cells, embryonic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. The term "donor cell" includes embryonic, fetal, pediatric, or adult cells or tissues, including but not limited to, stem cells and precursors (progenitor) cells.

Thus, donor cells of the invention can be myocardial cells, bone marrow cells, hematopoietic cells, lymphocytes, leukocytes, granulocytes, hepatocytes, monocytes, macrophages, fibroblasts, neural cells, mesenchymal stem cells, beta-islet cells, and combinations thereof, or cells capable of differentiating into those cells. In one embodiment, the donor cells are autologous cells, however, non-autologous cells, e.g., xenogeneic cells, may also be employed. In one embodiment, the donor cells are endothelial progenitor cells, $CD133^+$ cells, $CD34^+$ cells, mesenchymal stem cells, skeletal myoblasts, neural stem cells, pancreatic beta cells, cardiac stem cells or embryonic stem cells.

Stem cells may be isolated from any source known in the art and includes, but is not limited to, e.g., peripheral blood stem cells (PBSC), stem cells isolated from bone marrow; stem cells isolated from adipose tissue; mesenchymal stem cells, embryonic stem cells, $CD34^+$ cells, $CD34^-$ cells, $CD45^+$ cells, or combinations thereof). Stem cells which express one or more of the following antigens may be useful in the methods of the invention: CD34, CD133, ABCG2, Sca-1, Stro-1, nestin, PSA-NCAm, P75 neurotrophin, c-kit or CD30. Exemplary stem cells and methods of isolating them are described in, e.g., Fickert et al., *Osteoarthritis Cartilage,* 11:790 (2003), which discloses identification, quantification and isolation of human mesenchymal progenitor cells from osteoarthritic synovium; Meirelles et al., *Br. J. Haematol.,* 123:702 (2003), which discloses isolation, in vitro expansion, and characterization of mesenchymal stem cell from bone marrow; Pittenger et al., *Science,* 284:143 (1999), which discloses isolation, analysis, and differentiation of adult human mesenchymal stem cells from bone marrow; Lataillade et al., *Blood,* 95:756 (2000) or Handgretinger et al., *Bone Marrow Transplant,* 27:777 (2001), which disclose isolation, analysis, and purification of adult human peripheral blood $CD34^+$ progenitor cells; U.S. Pat. No. 6,667,034 which discloses isolation and differentiation of stem cells from human hematopoietic cells, i.e., from bone marrow and peripheral blood; and U.S. Pat. No. 6,261,549 which discloses isolation of human mesenchymal stem cells from peripheral blood; and Gepstein, *Circ. Res.,* 91:866 (2002), which discloses derivation of embryonic stem cells.

Typically, stem cells are purified from peripheral blood using methods known in the art including, e.g., immunomagnetic selection with the MACS system (Miltenyi Biotech, Tebu) or antibody-coated Dynabeads (Dynal Biotech, Oslo). A heterogenous population of cells may be contacted with antibody-coated magnetic beads. The antibody specifically binds to a cell surface marker differentially or preferentially expressed on the surface of a stem cell, thereby forming a complex between the beads and the stem cells in the heterogenous population. The labeled stem cells can then be isolated from the heterogenous cell population using methods known in the art including, e.g., flow cytometry.

For example, bone marrow is aspirated from the posterior iliac crest under a brief general anesthesia. Unselected BMCs are enriched under good manufacturing practice conditions by 4% gelatin-polysuccinate density gradient sedimentation as described in Wollert et al. (*Lancet,* 364:141 (2004)). $CD34^+$ cells may be immunomagnetically enriched from unselected BMCs by the CliniMACS$^{plus}$ System and CD34 antibodies from Miltenyi Biotech. The number of CD34+ cells in unselected BMC preparations and in CD34-enriched preparations may be determined by flow cytometry analysis (FACSCalibur, BD Biosciences) using an antibody from Beckman Coulter.

Alternatively, BMCs are isolated by Ficoll density gradient centrifugation. After two washing steps, cells are resuspended to yield a heterogeneous cell population including hematopoietic progenitor cells, but also other cell types (e.g., side population cells, stromal cells, and so on). Overall, a mean value of $5.5 \pm 3.9 \times 10^6$ CD34/CD45-positive cells may be infused per patient.

For CPCs, mononuclear cells from venous blood are suspended in medium supplemented with 1 ng/ml carrier-free human recombinant vascular endothelial growth factor (R&D, Wiesbaden, Germany), 0.1 µmol/L atorvastatin (Pfizer, Freiburg, Germany), and 20% human serum drawn from each individual patient. Cells are seeded at a density of $6.4 \times 10^5$ cells/mm² on fibronectin-coated dishes (Roche, Grenzach, Germany). After three days of cultivation, cells are detached with 0.5 mmol/L ethylenediamine-tetraacetic acid, washed twice, and re-suspended in a final volume of 10 ml of medium. The resulting cell suspension contains a heterogeneous population of progenitor cells, however, more than 90% of the cells show endothelial characteristics, as demonstrated by DiI-acetylated low-density lipoprotein-uptake and lectin binding and the expression of typical endothelial marker proteins including vascular endothelial growth factor-R2 (KDR) (ReliaTech, Braunschweig, Germany), endoglin (CD105) (NeoMarkers, Asbach, Germany), von Willebrand factor (Oncogene, Schwalbach, Germany), and platelet endothelial cell adhesion molecule-1 (PECAM-1/CD31) (Dianova, Hamburg, Germany) (Assmus et al., *Circulation*, 106: 3009 (2002); Dimmeler et al., *J. Clin. Invest.*, 108:391 (2001); Vasa et al., *Circulation*, 103:2885 (2001); Vasa et al., *Circ. Res.*, 89:1 (2001)).

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells are removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

Donor cells can be expanded in vitro to provide an expanded population of donor cells for administration. In addition, donor cells may be treated in vitro (ex vivo) to induce certain phenotypic characteristics, e.g., to induce proliferation or differentiation, to introduce one or more expression cassettes (transgenes) encoding a gene product, i.e., the donor cells may be recombinant cells. Thus, donor cells may be primed or preconditioned, e.g., treated with a cytokine or a mixture of cytokines or transformed with an expression cassette. Priming or preconditioning can facilitate homing of the donor cell to the tissue or site of interest and differentiation or transdifferentiation of the donor cell after it has homed to the injured tissue or site of interest.

In one embodiment, the donor cells are recombinant cells having an expression cassette. The expression cassette optionally includes at least one control element such as a promoter, optionally a constitutive promoter, an enhancer, or a transcription termination sequence. In one embodiment, a promoter is operably linked to an open reading frame encoding a gene product, e.g., a soluble therapeutic gene product, a cell membrane spanning gene product, an adhesion molecule and/or an activating molecule, e.g., TNFα. In one embodiment, the promoter may be an inducible promoter, for instance, one that is induced during homing with a drug, e.g., tetracycline. In one embodiment, the promoter and/or enhancer is one which is cell- or tissue-specific, e.g., cardiac cell-specific.

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Gene delivery vectors include, but are not limited to, isolated nucleic acid, e.g., plasmid-based vectors which may be extrachromosomally maintained, and viral vectors, e.g., recombinant adenovirus, retrovirus, lentivirus, herpesvirus including cytomegalovirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

Biocompatible Materials for Use with Agents of the Invention

The agents of the invention may be coated on and/or embedded in a biocompatible material which in turn may be coated on and/or embedded in a device. Biocompatible materials include polyacetic or polyglycolic acid and derivatives thereof, polyorthoesters, polyesters, polyurethanes, polyamino acids such as polylysine, lactic/glycolic acid copolymers, polyanhydrides and ion exchange resins such as sulfonated polytetrafluorethylene, polydimethyl siloxanes (silicone rubber) or combinations thereof.

Additionally, it is possible to construct biocompatible materials from natural proteins or materials which may be crosslinked using a crosslinking agent such as 1-ethyl-3-(3-dimethylamino-propyl)carbodiimide hydrochloride. Such natural materials include albumin, collagen, fibrin, alginate, extracellular matrix (ECM), e.g., xenogeneic ECM, hyaluronan, chitosan, gelatin, keratin, potato starch hydrolyzed for use in electrophoresis, and agar-agar (agarose).

In one embodiment, the material may include liposomes, a hydrogel, cyclodextrins, nanocapsules or microspheres. Thus, a biocompatible material includes synthetic polymers in the form of hydrogels or other porous materials, e.g., permeable configurations or morphologies, such as polyvinyl alcohol, polyvinylpyrrolidone and polyacrylamide, polyethylene oxide, poly(2-hydroxyethyl methacrylate); natural polymers such as gums and starches; synthetic elastomers such as silicone rubber, polyurethane rubber; and natural rubbers, and include poly[α(4-aminobutyl)]-1-glycolic acid, polyethylene oxide (Roy et al., *Mol. Ther.*, 7:401 (2003)), poly orthoesters (Heller et al., *Adv. Drug Delivery Rev.*, 54:1015 (2002)), silk-elastin-like polymers (Megeld et al., *Pharma. Res.*, 19:954 (2002)), alginate (Wee et al., *Adv. Drug Deliv. Rev.*, 31:267 (1998)), EVAc (poly(ethylene-co-vinyl acetate), microspheres such as poly (D,L-lactide-co-glycolide) copolymer and poly (L-lactide), poly(N-isopropylacrylamide)-b-poly(D,L-lactide), a soy matrix such as one crosslinked with glyoxal and reinforced with a bioactive filler, e.g., hydroxylapatite, poly(epsilon-caprolactone)-poly(ethylene glycol) copolymers, poly(acryloyl hydroxyethyl) starch, polylysine-polyethylene glycol, an agarose hydrogel, or a lipid microtubule-hydrogel.

In one embodiment, the biocompatible material includes but is not limited to hydrogels of poloxamers, polyacrylamide, poly(2-hydroxyethyl methacrylate), carboxyvinylpolymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols.

In some embodiments, the biocompatible polymeric material is a biodegradable polymeric such as collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), poly(dioxanone) (PPS) or cellulose derivatives such as cellulose acetate. In an alternative embodiment, a biologically derived polymer, such as protein, collagen, e.g., hydroxylated collagen, or fibrin, or polylactic-polyglycolic acid or a polyanhydride, is a suitable polymeric matrix material.

In another embodiment, the biocompatible material includes polyethyleneterephalate, polytetrafluoroethylene, copolymer of polyethylene oxide and polypropylene oxide, a combination of polyglycolic acid and polyhydroxyalkanoate, or gelatin, alginate, collagen, hydrogels, poly-3-hydroxybutyrate, poly-4-hydroxybutyrate, and polyhydroxyoctanoate, and polyacrylonitrilepolyvinylchlorides.

Other biocompatible materials include natural polymers such as starch, chitin, glycosaminoglycans, e.g., hyaluronic acid, dermatan sulfate and chrondrotin sulfate, collagen, and microbial polyesters, e.g., hydroxyalkanoates such as hydroxyvalerate and hydroxybutyrate copolymers, and synthetic polymers, e.g., poly(orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone. The incorporation of molecules such as tricalciumphosphate, hydroxyapetite and basic salts into a polymer matrix can alter the degradation and resorption kinetics of the matrix. Moreover, the properties of polymers can be modified using cross-linking agents.

In one embodiment, the biocompatible material is isolated ECM. ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like. The preparation and use of isolated ECM in vivo is described in co-pending, commonly assigned U.S. patent application Ser. No. Ser. No. 11/017,237, entitled "USE OF EXTRACELLULAR MATRIX AND ELECTRICAL THERAPY," filed on Dec. 20, 2004, which is hereby incorporated by reference in its entirety.

Exemplary Methods

The goal of any cell delivery strategy is to transplant sufficient numbers of cells into the region of interest and to achieve maximum retention of cells within that area. Retention may be defined as the fraction of transplanted cells retained in a target tissue or site for a period of time (minutes, hours or weeks). The local milieu is an important determinant of cell retention, as it will influence short-term cell survival and, if a transvascular approach is used, cell adhesion, transmigration through the vascular wall, and tissue invasion.

One embodiment of the present invention provides a method of targeting stem cells to injured cardiac tissues. The stem cells may be autologous to the patient with the cardiovascular disorder, or may be obtained from an allogeneic or xenogeneic donor. In patients receiving BMC, bone marrow aspirates may be obtained in the morning of the day of cell transplantation. In patients receiving CPC, 250 ml of venous blood is collected immediately after randomization (24 hours after the AMI), mononuclear cells are purified and ex vivo cultured for three days, and then re-infused into the infarct artery. In one embodiment, cells are activated by contact and movement over cultured endothelial cells prior to administration. In one embodiment, cells may be infused via an over-the-wire balloon catheter advanced into a stent previously implanted during the acute reperfusion procedure and inflated with low pressure to completely block blood flow for 3 minutes to allow for adhesion and potential transmigration of the infused cells through endothelium. This maneuver may be repeated three times to accommodate infusion of the total 10 ml donor cell suspension, interrupted by 3 minutes of reflow by deflating the balloon to minimize extensive ischemia. After completion of intracoronary cell transplantation, coronary angiography may be repeated to ascertain vessel patency, absence of embolization, and unimpeded flow of contrast material.

In one embodiment, unselected BMCs are infused into the infarct-related artery via the central lumen of an over-the-wire balloon catheter. To maximize the contact time of the BMCs with the microcirculation of the infarct-related artery, the balloon may be inflated inside the stent for about 3 minutes during the infusion. Additionally, BMCs may be infused during 3 to 4 additional coronary occlusions. Between occlusions, the coronary artery is reperfused for about 3 minutes.

Alternatively, unselected BMCs are injected via a right antecubital vein. Additionally, cells may be infused into the infarct-related artery.

In another embodiment, about 2.5-fold more bone marrow is aspirated to obtain more $CD34^+$ cells. $CD34^+$ cells are enriched from unselected BMCs, and infused into the infarct-related artery. Afterward, the CD34-depleted BMC fraction may be infused during 3 to 4 additional coronary occlusions.

Selective intracoronary application delivers a maximum concentration of cells homogeneously to the site of injury during first passage. Unselected BMCs, circulating blood-derived progenitors cells, and MSCs have been delivered via the intracoronary route in patients with AMI and ischemic cardiomyopathy. Cells are delivered through the central lumen of an over-the-wire balloon catheter during transient balloon inflations to maximize the contact time of the cells with the microcirculation of the infarct-related artery.

Exemplary Compositions

The present invention also relates to a pharmaceutical composition including one or more agents that enhance or inhibit expression or activation of adhesion molecules in donor cells, endogenous tissue, or both, in a pharmaceutically acceptable carrier. In some embodiments, the pharmaceutical composition includes donor cells, and one or more agents that enhance expression or activation of adhesion molecules in the donor cells, in endogenous tissue, or both. In other embodiments, the pharmaceutical composition includes agents that inhibit or block expression or activation of adhesion molecules in endogenous tissue. In some therapeutic applications, compositions are administered to a patient suffering from a disease (e.g., cardiovascular disease), in an amount sufficient to cure or at least partially arrest the disease and its complications, i.e., by repairing injured myocardium. An amount adequate to accomplish this is defined as a therapeutically effective dose. Amounts effective for this use depend on the severity of the cardiovascular disease and the general state of the patient's health.

The pharmaceutical compositions of the present invention (i.e., compositions including donor cells and/or agents that enhance or inhibit expression or activation of adhesion molecules) may be administered by any means known in the art. Preferably, the compositions are suitable for parenteral administration (e.g., intravenous, intraperitoneal). The compositions of the invention may also be administered subcutaneously, into vascular spaces, or into joints, e.g., intraarticular injection.

Single or multiple administrations of the compositions may be administered depending on the dosage and frequency as required and tolerated by the patient. In any event, the composition should provide a sufficient quantity of the donor cells to effectively treat the patient, i.e., to repair or augment repair of injured myocardium.

Preferably, the compositions for administration include a solution of the composition and a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, sterilization techniques known in the art. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The composition having donor cells and/or an agent that enhances or inhibits expression or activation of adhesion molecules may also formulated in microspheres, liposomes or other microparticulate delivery systems. The concentration of composition having donor cells or an agent that enhances or inhibits expression or activation of adhesion molecules in these formulations can vary widely, and will be selected primarily based on fluid volumes, viscosities, body weight and the like in accordance with the particular mode of administration selected and the patient's needs.

A typical pharmaceutical composition comprising donor cells for intravenous administration may be about $10^5$ to about $4\times10^6$ cells, about $5\times10^5$ about $3\times10^6$ cells, or about $10^6$ to about $2.5\times10^6$ cells, or about $1.5\times10^6$ to about $2.0\times10^6$ cells per patient per day, or about 0.5 to about $5.0\times10^6$ cells/kg, or up to about $1\times10^{10}$ to about $5\times10^{10}$ cells per patient. Methods for preparing parenterally administrable compositions will be known or apparent to those skilled in the art and are described in more detail in such publications as Remington's Pharmaceutical Science, 17th Ed., Mack Publishing Co., Easton, Pa., (1985).

Typically, the pharmaceutical compositions having donor cells or an agent that enhances or inhibits expression or activation of adhesion molecules are administered in a therapeutically effective dose over either a single day or several days by daily intravenous infusion. The dose will be dependent upon the properties of the composition having donor cells or an agent that enhances or inhibits expression or activation of adhesion molecules employed, e.g., its activity and biological half-life, the concentration of the composition having donor cells or an agent that enhances or inhibits expression or activation of adhesion molecules in the formulation, the site and rate of dosage, the clinical tolerance of the patient involved, the extent of disease afflicting the patient and the like as is well within the skill of the physician.

The compositions may be administered in solution. The pH of the solution should be in the range of pH 5 to 9.5, preferably pH 6.5 to 7.5. The compositions thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of the compositions may also contain a salt, such as sodium chloride or potassium chloride in a concentration of 50 to 150 mM. An effective amount of a stabilizing agent such as albumin, a globulin, a detergent, a gelatin, a protamine or a salt of protamine may also be included and may be added to a solution containing the immunoconjugate or to the composition from which the solution is prepared. In some embodiments, systemic administration of the composition having donor cells is typically made every two to three days or once a week. Alternatively, daily administration is useful. Usually administration is by intravascular infusion.

The compositions described herein (i.e., donor cells or an agent that enhances or inhibits expression or activation of adhesion molecules) can be administered to a patient in conjunction with other therapies, e.g., therapies for cardiovascular disease. For example, the compositions may be administered in conjunction with angioplasty to promote repair of injured cardiac tissue. The compositions may be administered prior to the angioplasty, contemporaneous with the angioplasty, or subsequent to the angioplasty.

Agents and Treatments Useful in the Methods and Devices

Agents and treatments useful in the methods of the invention include those which alter, e.g., enhance or inhibit, cell surface molecule expression or activation on target tissue or cells, e.g., ex vivo, at a particular physiological site, or both. Agents or treatments useful in the methods of the invention include but are not limited to ischemic conditions, pacing, irritants, e.g., LPS, TNF-α or other cytokines such as IL-1, IL-6 or IL-8, including agents that enhance adhesion molecule expression or activation on donor cells, endogenous cells or both. Agents that modulate the expression or activation of adhesion molecules, e.g., those in Table 1, on target tissue or cells, agents including but not limited to NSAIDS, glucocorticoids, agents that modulate, e.g., enhance or inhibit, cytokines or their receptors, peptides, e.g., RGD or KTS based peptides or mimetics thereof, or antibodies, i.e., neutralizing, agonistic or antagonistic antibodies specific for adhesion molecules such as selecting, ICAMS, and VCAMS (see Verbeuren et al., *Microcirc.*, 7:541 (2000), Wahl et al., *Curr. Op. Clin. Nutr. Meta. Care*, 2:109 (1999), Buchner et al., *Imm. Allergy Clin. North Am.*, 24:615 (2004), Lutters et al., *Curr. Op. Libidology*, 15:545 (2004)), including neutralizing and antagonistic antibodies of adhesion molecules to block adhesion or agonistic antibodies of adhesion molecules to activate or enhance adhesion, and agents disclosed in U.S. published applications 20060030575; 20050226873; 20050187611; 20050059669; 2005026917; 20040086519; 20040077684; 20040063934; 20040077638; 20030186967; 2003018633; 20030171368; and U.S. Pat. Nos. 6,663,863; 6,586,187; 6,541,116; 6,461,821; 6,214,334; 6,185,953; 5,961,483; 5,935,598; 5,718,892; 5,691,423; and 5,196,403.

Compounds that modulate cadherin are disclosed in U.S. Pat. Nos. 6,907,238; 6,914,144; 6,962,969; 6,806,255; 6,203,788; and 6,569,996.

TABLE 1

| Adhesion molecules | Other names | Ligands |
| --- | --- | --- |
| Selectins/ligands | | |
| P-selectin | CD62P, GMP140 | PSGL-1, Lewis X, CD24 |
| E-selectin | CD62D, ELAM1 | ESL-1, Lewis X, PSGL-1, Lyset |
| L-selectin | CD62L | Lewis X, CD 34, PSGL-1, GlyCAM |
| E-selectin ligand 1 | ESL-1 | E-selectin |
| P-selectin ligand 1 | CD162, PSGL-1 | P-, L-, E-selectin PNAd, cutaneous lymphocyte antigen (CLA), CD15 (Sialyl-Lewis X) |
| Ectoenzymes and other adhesion molecules | | |
| VAP-1 | semicarbazide-sensitive amino oxidase (SSAO), AOC-3, HPAO, and membrane, copper amine oxidase | amine groups |
| Retina-specific amine oxidase | AOC2 | amine groups |
| CD26 | EC3.4.14.5, adenosine deaminase binding protein, ADA binding protein, dipeptidylpeptidase IV, DPPIV ectoenzyme | adenosine deaminase, collagen, CD45 |
| CD38 | T10, ADP-ribosylcyclase; cyclic ADP-ribose hydrolase | CD31, hyaluronic acid |
| CD73 | Ecto-5'-nucleotidase | |
| mannose receptor | | collagen |
| clever-1 (common lymphatic endothelial and vascular receptor-1) | stabilin-1, FEEL-1 | |
| CD40 | Bp50 | CD40L |
| CD44 | ECMRIII, HCAM, HUTCH-1, Hermes, Lu, In-related, Pgp-1, gp85 | Hyaluronan, MIP-1β, osteopontin, ankyrin, fibronectin |
| Immunoglobulins | | |
| ICAM-1 | CD54 | αLβ2, αMβ, αXβ2 |
| ICAM-2 | CD102 | αLβ2, αMβ |
| ICAM-3 | CD50 | αLβ2, αDβ2, DC-SIGN |
| VCAM-1 | CD106 | α4β1, α4β7 αDβ2 |
| PECAM-1 | CD31 | PECAM-1, Vβ3 |
| NCAM-1 | LFA-3 (lymphocyte function associated antigen-3), CD58 | CD2 |
| MAdCAM-1 (mucosal vascular addressin cell adhesion molecule-1) | MACAM-1, mucosal addressin cell adhesion molecule-1 precursor | |
| JAM-2 (junctional adhesion molecule-2), | C21orf43, HGNC1284, JAMA-A, JAM-B, Junctional adhesion molecule B precursor, PRO245, UNQ219/PRO245, vascular endothelial junction-associated molecule, VE-JAM, CD322 | |
| JAM-1 (junctional adhesion molecule-1) | Jcam-1, JAM-A, Jcam, Junctional adhesion molecule A precursor, F11 receptor, Ly106, AA638916, 913004G24, BV11 antigen, ESTM33, CD321 | |

TABLE 1-continued

| Adhesion molecules | Other names | Ligands |
| --- | --- | --- |
| Mucins | | |
| Mad-CAM-1 | | α4β7 integrin, L-selectin |
| GlyCAM-1 (glycosylation dependent cell adhesion molecule-1) | | L-selectin |
| Integrins | | |
| Integrin α2/β1 | CD49b/CD29, VLA2 | Collagen, laminin |
| Integrin α4/β1 | CD49d/CD29, VLA4 | VCAM-1, FN |
| Integrin αL/β2 | CD11a/CD18, LFA1 | ICAMs |
| Integrin αM/β2 | CD11b/CD18, Mac1 | ICAMs, iC3b FX, FG |
| Integrin αX/β2 | CD11c/CD18 | ICAM-1, FG, iC3b, CD23 |
| Integrin αD/β2 | CD11d/CD18 | ICAM-3, VCAM-1 |
| Integrin α2B/α3 | GPIIb/IIIa | vWF, FN, FG, VN, thrombospondin |
| Integrin αV/β3 | VNR, CD51/CD61 | PECAM-1, WN, FN, FG, vWF, VN |
| Integrin αV/β5 | | |
| Integrin α4/β7 | | |

Agents useful to inhibit localization of endogenous circulating stem cells, or to inhibit or treat inflammation, restenosis or oxidative stress, include inhibitors of VAP-1 or SSAO, e.g., hydrazine derivatives, e.g., aryl(alkyl)hydrazines, arylalkylamines, propenyl- and proparyl-amines, oxazolidinones and haloalkylamines, including but not limited to 3-halo-2-phenylallylamines, semicarbazide, hydroxylamine, propargylamine, pyridoxamine, (+)mexiletine, B-24 (3,5-diethoxy-4-aminomethylpyridine), amiflamine (FLA 336(+)), FLA336 (−), FLA788 (+), FLA668 (+), MDL-72145 ((E)-2-(3,4-dimethyloxyphenyl)-3-fluoroallyamine, MDL-72974A ((E)-2-(4-fluorophenethyl)-3-fluoroallylamine hydrochloride), iproniazid, phenelzine, procarbazine (N-isopropyl-alpha-(2-methylhydrazino)-p-toluamide hydrochloride), hydralazine, carbidopa, benserazide, aminoguanidine (pimagedine), 2 bromoethylamine, and carbocyclic hydrazino compounds.

In one embodiment, inhibitors of VAP-1 or other copper containing amine oxidases such as SSAO useful in the devices and methods of the invention include but are not limited to those disclosed in U.S. Pat. Nos. 6,982,286, 6,624,202, and 6,066,321; U.S. published application 20060128770 (thiazole derivatives), 20060025438, 20050096360, 20040259923, 20040236108 (carbocyclic hydrazine), 20040106654, 20030125360, 20020173521, and 20020198189; Koskinen et al. (*Blood,* 103:3388 (2004)), Lazar et al. (*Acta Pharma. Hungarica,* 74:11 (2004), peptide inhibitors in Yegutkin et al. (*Eur. J. Immunol.,* 34:2276 (2004)), Wang et al. (*J. Med. Chem.,* 49:2166 (2006)), e.g., compounds 4a and 4c therein, esterified pectins such as those disclosed in Hou et al. (*J. Ag. Food Chem.,* 51:6362 (2003)), e.g., DE65T4, DE94T18, DE25T4, and DE94T4, and includes anti-VAP antibodies such as those described in U.S. Pat. Nos. 5,580,780 and 5,512,442, and Koskinen et al. (*Blood,* 103:3388 (2004)), Arvilemmi et al. (*Eur. J. Immunol.,* 26:825 (1996)), Salmi et al. (*J. Exp. Med.,* 178:2255 (1993)), and Kirton et al. (*Eur. J. Immunol.,* 35:3119 (2005)). Other inhibitors of VAP-1 include, but are not limited to, phenylhydrazine, 5-hydroxytryptamine, 3-bromopropylamine, N-(phenyl-allyl)-hydrazine HCl (LJP-1207), 2-hydrazinopyridine, TNF-α, MDL-72274 ((E)-2-phenyl-3-chloroallylamine hydrochloride), MDL-72214 (2-phenylallylamine), mexiletine, isoniazid, an endogeneous molecule, e.g., see Lizcano et al., *J. Neurol. Trans.,* 32:323 (1990) including one about 500 to 700 MW (see Obata et al., *Neurosci. Lett.,* 296:58 (2000)), imipramine, maprotiline, zimeldine, nomifensine, azoprocarbazine, monomethylhydrazine, dl-alpha methyltryptamine, dl-alpha methylbenzylamine, MD780236 (Dostert et al., *J. Pharmacy & Pharmacol.,* 36:782 (2984)), 2-(dimethyl(2-phenylethyl)silyl) methanamine, cuprozine, alkylamino derivatives of 4-aminomethylpyridine (Bertini et al., *J. Med. Chem.,* 48:664 (2005)), and kynuramine. Preferred inhibitors are selective SSAO inhibitors, e.g., agents that inhibit SSAOs at least 2-fold more than MAOs. Inhibitors may be reversible, competitive, noncompetitive or irreversible inhibitors.

Exemplary Devices For Donor Cells and Agents that Alter Expression of Adhesion Molecules Devices useful for administering agents and/or activating, administering and/or implanting donor cells, to an organ or body part, include a lumen, and may be, but are not limited to, a catheter, needle, stent, e.g., be made of stainless steel, Nitinol (NiTi), or chromium alloy and biodegradable materials, a stent graft, a synthetic vascular graft, e.g., one made of a cross-linked PVA hydrogel, polytetrafluoroethylene (PTFE), expanded polytetrafluoroethylene (ePTFE), porous high density polyethylene (HDPE), polyurethane, and polyethylene terephthalate, or biodegradable materials, a pacemaker, lead, e.g., pacemaker lead, defibrillator, a hemodialysis catheter, or a drug delivery port. The medical device can be made of numerous materials depending on the device. In one embodiment, the device is coated with one or more agents. For example, adhesion molecules or peptides thereof may be coated on the inside lumen of a catheter via a linker, e.g., polyethylene glycol (PEG) based linker. Thus, as cells are delivered to a mammal, they are activated by interaction with the adhesion molecules or peptides thereof that are coated on the lumen of the catheter.

FIG. 1 illustrates stages of homing (localization or targeting) of donor cells 100 to host tissue including endothelial cells 105. Donor cells 100A-D each illustrate a donor cell in a different stage of the homing process. In a rolling stage, donor cell 100A is rolling over endothelial cells 105 expressing adhesion molecules 106 and 107 on the surface of the tissue. In an activation stage, donor cell 100B is activated to express or activate adhesion molecules 101 and 102. Once one or more integrins are in a high affinity state (an adhesion stage) (102B), donor cell 100C is bound to endothelial cells 105. In a transendothelial migration stage, donor cell 100D migrates across endothelial cells 105 into the host tissue. Exemplary devices discussed below with references to FIGS.

2-13 include specific examples of devices that promote interactions between donor cells 100 and endothelial cells 105 to increase the number of donor cells 105 at a particular physiological site.

Figure 2:
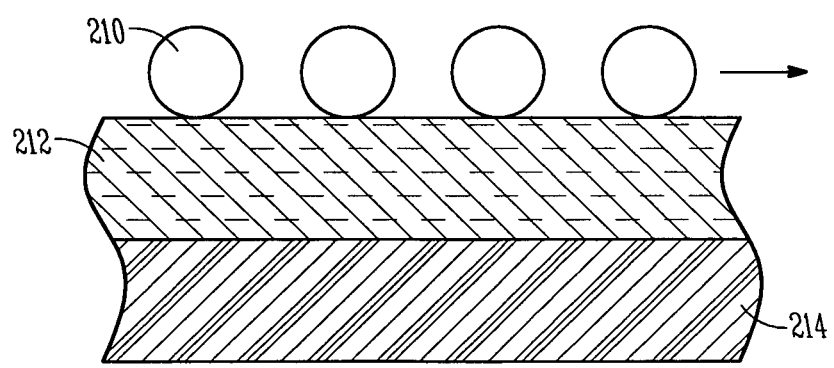
FIG. 2 is an illustration of an embodiment of an interaction surface on a surface portion of a device.

FIG. 2 is an illustration of an embodiment of an interaction surface 212 on a surface portion 214 of a device. The device includes at least a portion configured to enhance the expression or activation of adhesion molecules on donor cells 210 which in turn enhances targeting (localization) and extravasation of donor cells to host tissue including endothelial cells.

In various embodiments, interaction surface 212 includes one or more agents coated on surface portion 214. In another embodiment, one or more agents are released, e.g., via passive or active means, from the surface. The one or more agents enhance targeting of donor cells 210 as donor cells 210 roll over interaction surface 212. In one embodiment, donor cells 210 are stem cells. In one embodiment, interaction surface 212 is an activation surface, and the one or more agents include one or more agents that enhance localization and/or extravasation of donor cells. In a specific embodiment, the one or more agents increase the expression of adhesion molecules on the donor cells. Examples of such activation agents include activated endothelial cells and activating molecules such as receptors, chemokines, antibodies, peptides, or other proteins including enzymes and/or glycosylated proteins, particular macroscopic surface structures (e.g., ridges to create turbulence), or nanoscale topographic structures with features on the same scale as in a native activating environment. In another specific embodiment, the one or more agents increase expression of adhesion molecules on the surface of the endothelial cells in the host tissue. Examples of such activation agents include but are not limited to adhesion molecules and cytokines.

In another embodiment, interaction surface 212 is an inhibitory surface, and the one or more agents include one or more agents that inhibit or minimize activation, localization and/or extravasation of circulating endogenous cells. In another embodiment, interaction surface 212 is an inhibitory surface without addition of the one or more agents. In a specific embodiment, the one or more inhibitory agents block the adhesion of circulating endogenous cells. Examples of such inhibitory agents include but are not limited to a vascular adhesion protein-1 (VAP-1) inhibitor, such as a semicarbazide sensitive amine oxidase (SSAO) inhibitor. In a specific embodiment, the one or more inhibitory agents include an agent that inhibits or prevents restenosis.

Surface portion 214 is the portion of the device including a surface on which interaction surface 212 is coated or otherwise formed. In one embodiment, the device is an in vitro cell treatment device including a container to contain donor cells 210. The container includes surface portion 214. In another embodiment, the device is an in vitro cell treatment device including a lumen to allow passage of donor cells 210. The lumen includes surface portion 214. In another embodiment, the device is an in vitro cell treatment device including a circulation pathway to allow circulation of donor cells 210. Surface portion 214 is incorporated into the circulation pathway. In another embodiment, the device is a percutaneous injection device that allows for injection of donor cells 210, such as a delivery catheter, a syringe, or a needle. The percutaneous injection device includes a lumen to allow passage of donor cells. The lumen includes surface portion 214. In another embodiment, the device is an implantable device such as a bead, a transvascular lead, or an intravascular stent. The implantable device includes a portion that is a surface portion 214.

Figure 3:
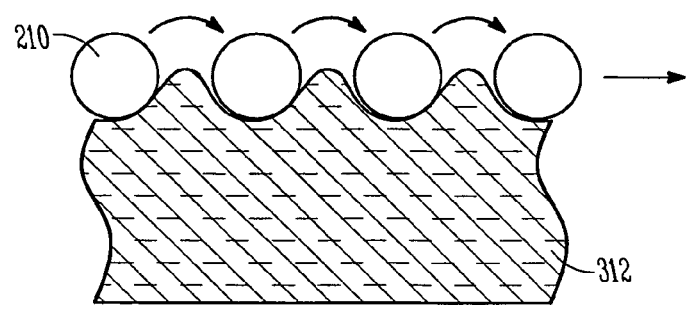
FIG. 3 is an illustration of a specific embodiment of the interaction surface.

FIG. 3 is an illustration of an embodiment of an interaction surface 312. Interaction surface 312 is a specific embodiment of interaction surface 212 and may be a surface that enhances or inhibits adhesion molecule expression or activation (an activation surface and inhibitory surface, respectively). Interaction surface 312 has a structure configured to increase the degree of interaction between the one or more agents and donor cells 210 as donor cells 210 roll over interaction surface 312. In a specific embodiment, the one or more agents are coated on surface portion 214 in a way that forms a rough surface being interaction surface 312.

Figure 4:
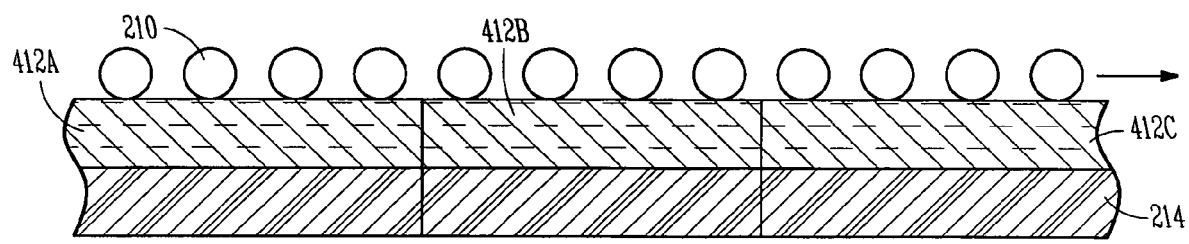
FIG. 4 is an illustration of an embodiment of the interaction surface including multiple interaction surface regions.

FIG. 4 is an illustration of an embodiment of an interaction surface 412 including multiple interaction surface regions 412A-C. Interaction surface 412 is a specific embodiment of interaction surface 212 and may be an activation surface or an inhibitory surface. Interaction surface regions 412A-C each include one of a plurality of agents that regulate the localization and/or extravasation of donor cells 210. In one embodiment, interaction surface regions 412A-C are arranged to allow donor cells 210 to roll over each of interaction surface regions 412A-C in a predetermined order to allow multiple steps of activation according to a predetermined activation sequence.

Figure 5:
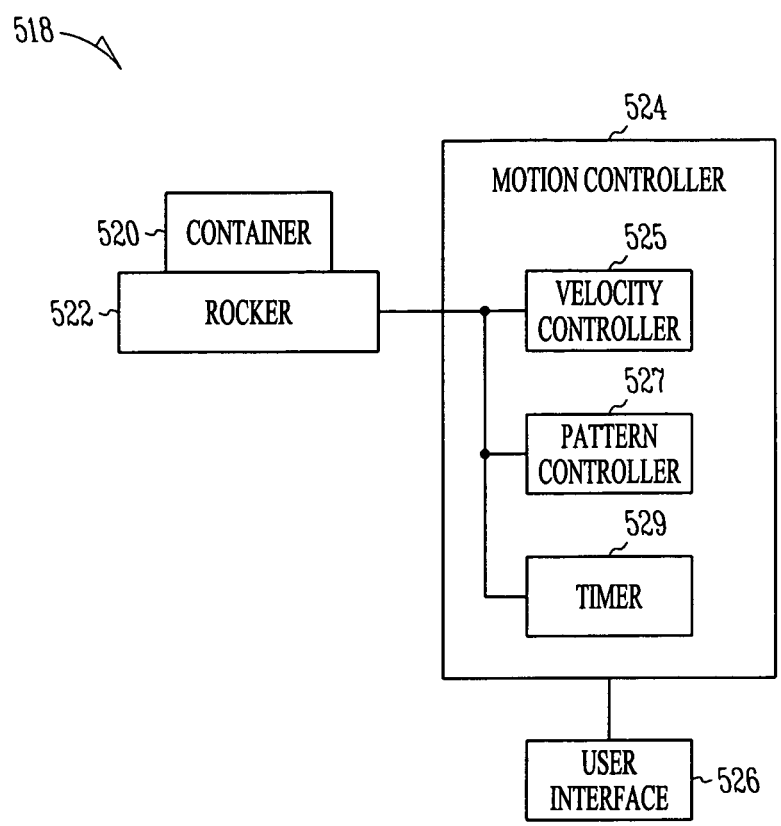
FIG. 5 is a block diagram illustrating an embodiment of a cell treatment system including the interaction surface.

FIG. 5 is a block diagram illustrating an embodiment of a cell treatment system 518 for in vitro cell treatment of donor cells prior to their administration into a body in a cell therapy. System 518 includes a container 520, a rocker 522, a motion controller 524, and a user interface 526. Container 520 contains donor cells and includes an activation surface being a specific embodiment of interaction surface 212. Rocker 522 creates a motion of container 520 that causes the donor cells contained in container 520 to roll over the activation surface. Motion controller 524 controls the motion of container 520 and includes a velocity controller 525, a pattern controller 527, and a timer 529. Velocity controller 525 controls the velocity of the motion of container 520. Pattern controller 527 controls the pattern of the motion of container 520. Timer 529 controls the timing of the motion of container 520, including when to start and stop the motion. User interface 526 allows a user to control the velocity, pattern, and timing of the motion of container 520. In one embodiment, user interface 526 allows the user to program a sequence of one or more motions of container 520 each including a velocity, a pattern, a starting time, and a duration or ending time.

Figure 6:
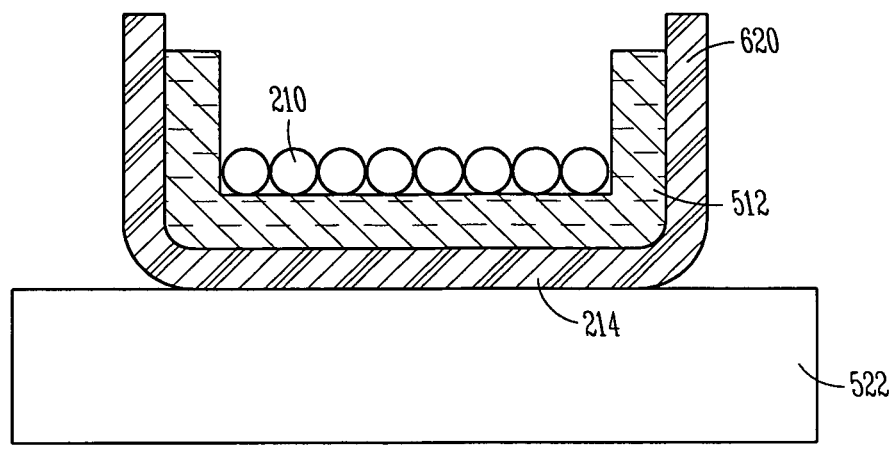
FIG. 6 is an illustration of a specific embodiment of portions of the treatment system of FIG. 5 with a dish including the interaction surface.

FIG. 6 is an illustration of a specific embodiment of portions of treatment system 518 including a dish 620, which is a specific embodiment of container 520. An activation surface 512 is coated on surface portion 214, which includes a bottom and/or side portion of dish 620. Activation surface 512 is a specific embodiment of interaction surface 212 and includes one or more activation agents that enhance localization and/or extravasation of the donor cells. In one embodiment, the one or more activation agents increase the expression of adhesion molecules on the donor cells.

Figure 7:
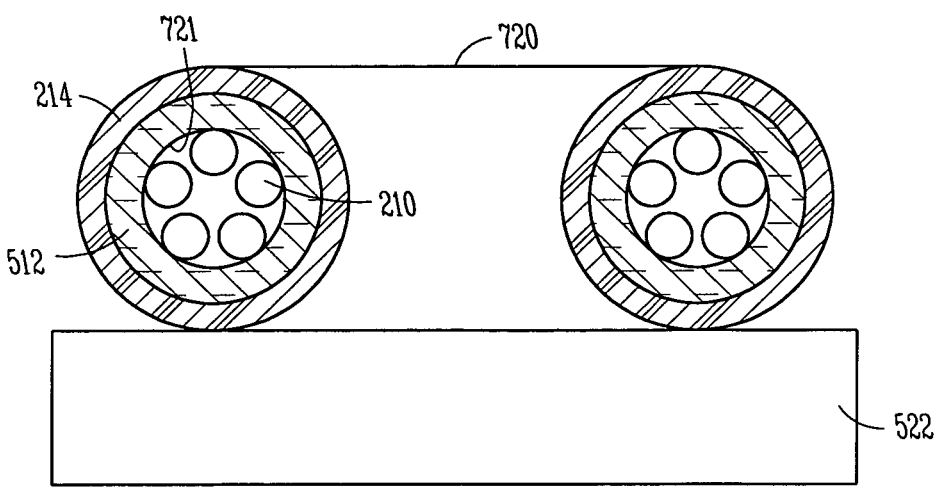
FIG. 7 is an illustration of a specific embodiment of portions of the treatment system of FIG. 5 with a circular tube including the interaction surface.

FIG. 7 is an illustration of a specific embodiment of portions of the treatment system 518 including a circular ("donut-shaped") tube 720, which is another specific embodiment of container 520. Activation surface 512 is formed on surface portion 214, which includes at least a portion of an interior wall 721 of circular tube 720. In one embodiment, surface portion 214 includes the entire interior wall 721. That is, activation surface 512 covers the entire interior wall of circular tube 720.

Figure 8:
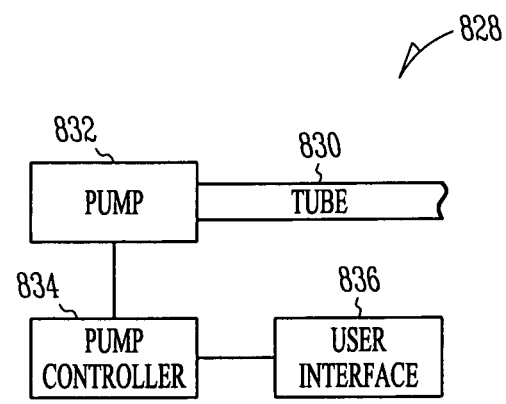
FIG. 8 is a block diagram illustrating an embodiment of another cell treatment system including the interaction surface.

FIG. 8 is a block diagram illustrating an embodiment of a cell treatment system 828. In one embodiment, system 828 represents portions of a system for in vitro cell treatment of donor cells prior to their administration into a body in a cell therapy. In another embodiment, system 828 represents portions of a system for delivering the donor cells into the body. System 828 includes an elongate tube 830, a pump 832, a pump controller 834, and a user interface 836. Elongate tube 830 includes a lumen configured to allow passage of the donor cells. Activation surface 512 is formed on at least a portion of the lumen. Pump 832 is connected to elongate tube 830 to pump the donor cells through the lumen of elongate tube 830. Pump controller 834 controls the speed of the passage of the donor cells through the lumen of elongate tube 830, and user interface 836 allows a user to control that speed. In one embodiment, system 828 represents a syringe-plunger system, with elongate tube 830 representing the body of the syringe and pump 832 representing the plunger.

Figure 9:
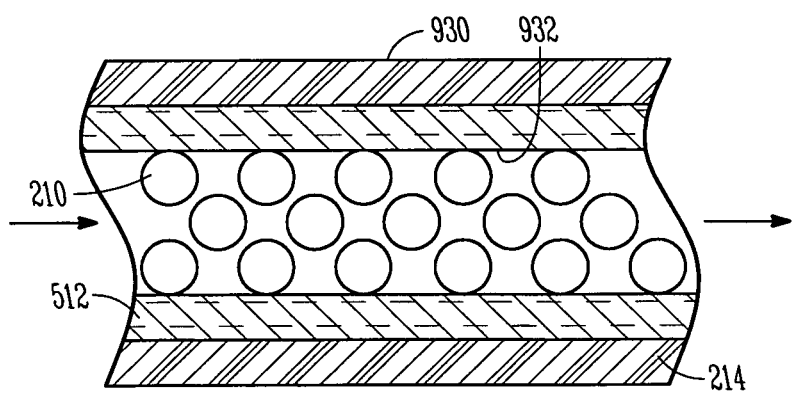
FIG. 9 is an illustration of a specific embodiment of portions of the treatment system of FIG. 8 with a tube including the interaction surface.

FIG. 9 is an illustration of an embodiment of a portion of an elongate tube 930, which is a specific embodiment of elongate tube 830. Elongate tube 930 includes a lumen 932 to allow passage of donor cells 210. At least a portion of lumen 932 constitute surface portion 214, on which activation surface 512 is formed.

In one embodiment, elongate tube 930 is part of a percutaneous transluminal catheter used to inject donor cells 210. In another embodiment, elongate tube 930 is part of a syringe used to inject donor cells 210. In another embodiment, elongate tube 930 is part of a hollow needle used to inject donor cells 210. In another embodiment, elongate tube 930 is part of an in vitro cell treatment system.

Figure 10:
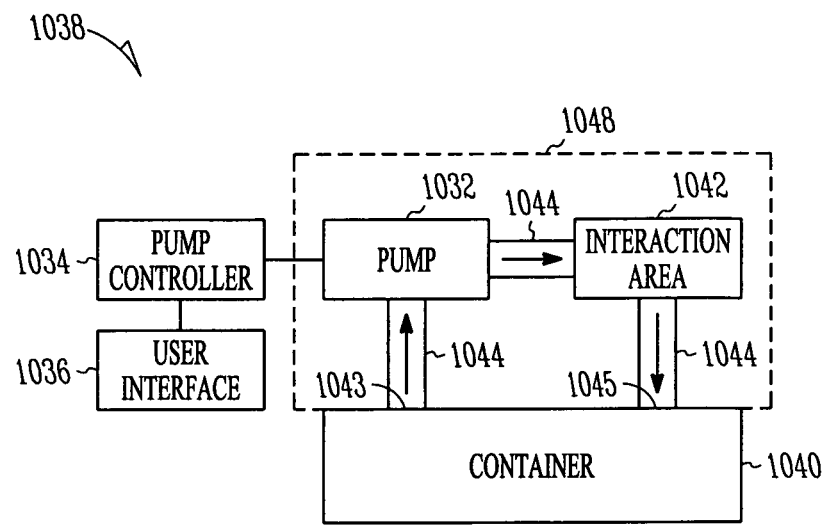
FIG. 10 is a block diagram illustrating an embodiment of another cell treatment system including the interaction surface.

FIG. 10 is a block diagram illustrating an embodiment of a cell treatment system 1038. In one embodiment, system 1038 represents portions of a system for in vitro cell treatment of donor cells prior to their administration into a body in a cell therapy. In another embodiment, system 1038 represents portions of a system for delivering the donor cells into the body. System 1038 is a fluid circulating system that includes a container 1040, a circulation pathway 1048, a pump controller 1034, and a user interface 1036. Container 1040 contains the donor cells in a fluid. In one embodiment, container 1040 is a reservoir of a cell delivery system for injecting the donor cells into the body. Circulation pathway 1048 allows for passage of the donor cells and the fluid and includes an entrance 1043, an exit 1045, a pump 1032, and an interaction area 1042. Entrance 1043 and exit 1045 include openings of tubing 1044. The donor cells and the fluid enter circulation pathway 1048 from container 1040 through entrance 1043 and return to container 1040 from circulation pathway 1048 through exit 1045. Pump 1032, which locates between the entrance and the exit, pumps the donor cells and the fluid through circulation pathway 1048. Interaction area 1042 includes activation surface 512 such that the donor cells roll over activation surface 512 when passing through circulation pathway 1048. Pump controller 1034 controls the speed of movement of the donor cells through circulation pathway 1048, and user interface 1036 allows a user to control that speed.

In one embodiment, interaction area 1042 is formed by forming activation surface 512 on a portion of the interior wall of tubing 1044. In this embodiment, elongate tube 930 as illustrated in FIG. 9 represents at least a portion of tubing 1044.

Figure 11:
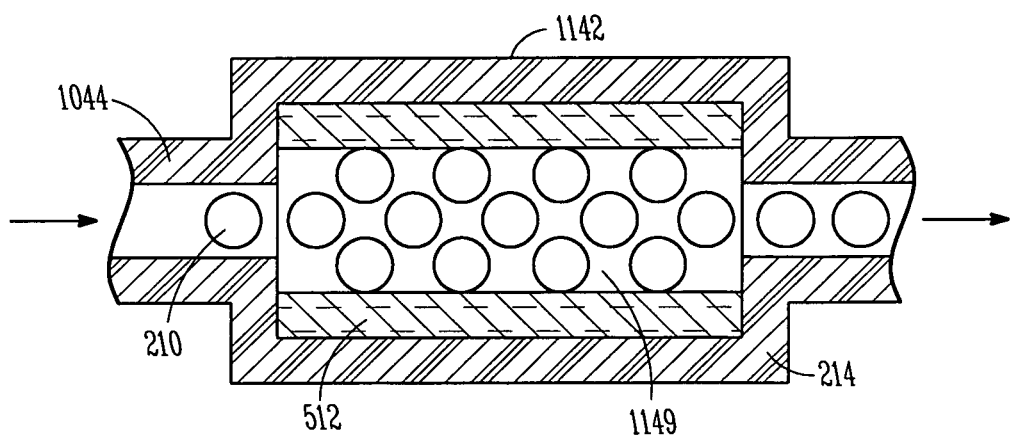
FIG. 11 is an illustration of a specific embodiment an interaction area of the cell treatment system of FIG. 10 including the interaction surface.

FIG. 11 is an illustration of an embodiment of an interaction area 1142, which is a specific embodiment of interaction area 1042. Interaction area 1142 is coupled between segments of tubing 1044 and includes a chamber 1149. Activation surface 512 is formed at least a portion of the wall of chamber 1149 that constitutes surface portion 214.

Figure 12:
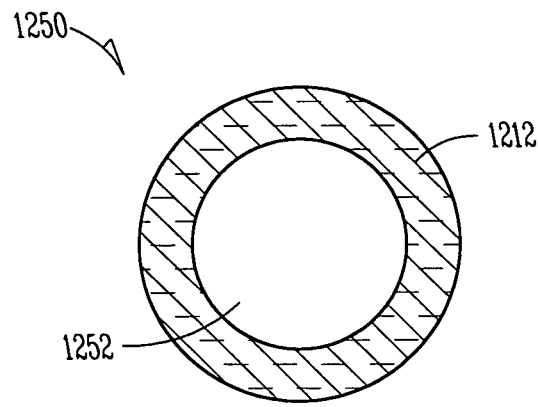
FIG. 12 is an illustration of an embodiment of an article including the interaction surface.

FIG. 12 is an illustration of an embodiment of an article 1250 for administration into a body to treat host tissue including endothelial cells. Article 1250 includes a bead 1252 such as a microsphere or nanosphere having an activation surface, e.g., one coated with one or more agents 1212. Bead 1252 is made of biocompatible and optionally biodegradable material such as alginate or those disclosed in U.S. Pat. No. 6,120,805, the disclosure of which is incorporated by reference herein in its entirety. Activation surface 1212 includes one or more agents coated on biodegradable bead 1252. The one or more agents enhance expression of adhesion molecules on surface of the host endothelial cells. Examples of the one or more agents include adhesion molecules and cytokines. In one embodiment, article 1250 (the coated biodegradable bead) has a size suitable for administration into the body using an injection device configured for localized agent delivery, such as a percutaneous transluminal catheter or a hollow needle. In one embodiment, article 1250 has an approximately spherical shape with a diameter in a range of approximately 10 nanometers to approximately 10 micrometers. In a specific embodiment, the diameter is between about 200 and about 2000 nanometers.

In one embodiment, a plurality of biodegradable beads each coated with the one or more agents are administrated into the body before the administration of the donor cells into the body. In another embodiment, a plurality of biodegradable beads each coated with the one or more agents are mixed with the donor cells. The mixture is then administrated into the body.

Figure 13:
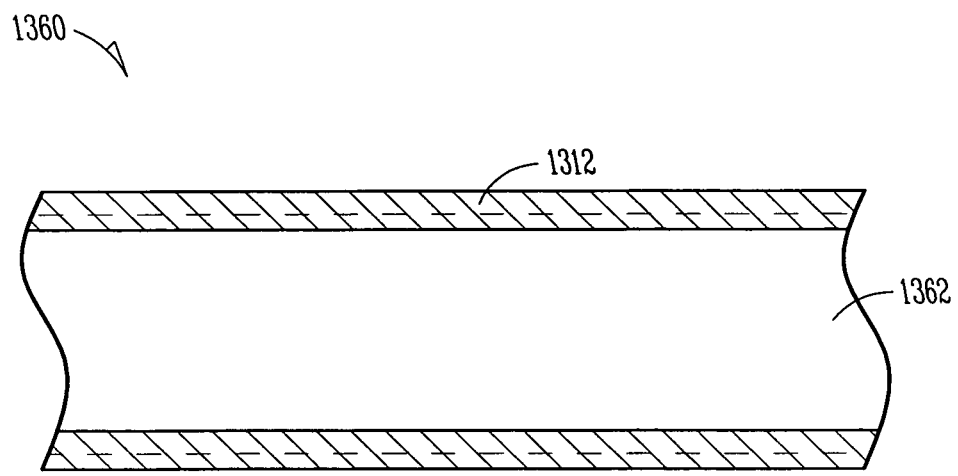
FIG. 13 is an illustration of an embodiment of an intravascular device including the interaction surface.

FIG. 13 is an illustration of an embodiment of a portion of an intravascular device 1360. Examples of intravascular device 1360 include a stent, such as a coronary stent, and a transvenous lead, such as a cardiac pacing or defibrillation lead. Intravascular device 1360 includes a surface portion 1362 on which an inhibitory surface 1312 is formed. Inhibitory surface 1312 includes the one or more inhibitory agents that inhibit localization and/or extravasation of endogenous circulating cells. The one or more inhibitory agents block the adhesion of the endogenous circulating cells. In one embodiment, the one or more inhibitory agents include an agent that inhibits or prevents restenosis, which agent is coated on at least a portion of the coronary stent. Examples of such inhibitory agents include a vascular adhesion protein-1 (VAP-1) inhibitor, for instance, a SSAO inhibitor. Specific examples of SSAO inhibitors include but are not limited to semicarbazide, hydroxylamine, propargylamine, pyridoxamine, (+)mexiletine, B-24, FLA 336, MDL-72145, MDL-72974A, iproniazid, phenelzine, procarbazine, hydralazine, carbidopa, benserazide, aminoguanidine, and 2 bromoethylamine, and carbocyclic hydrazine compounds.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A device adapted to deliver donor cells with enhanced localization to host tissue including endothelial cells in a body, comprising:
    an implantable delivery device configured to deliver the donor cells to the lumen of a vessel in the body and having a lumen with a surface portion including activated endothelium applied to the surface portion which has ridges configured to promote interaction between the activated endothelium and the donor cells so as to enhance the localization, extravasation, or both, of the donor cells by activating adhesion molecules on the donor cells or increasing expression of adhesion molecules on the donor cells relative to donor cells in the absence of the activated endothelium and ridges.

2. The device of claim 1 wherein the activated endothelium activates adhesion molecules on donor cells administered via the device.

3. The device of claim 1 wherein the activated endothelium increases expression of adhesion molecules on donor cells administered via the device.

4. The device of claim 1 wherein the implantable device comprises a percutaneous injection device comprising a catheter configured to allow injection of donor cells via the lumen having the surface portion.

5. A device for treating hematopoietic donor cells used in cell therapy, comprising:
   a surface portion; and
   an activation surface including different agents applied to the surface portion, wherein the different agents increase expression or activation of adhesion molecules on hematopoietic donor cells, the activation surface having ridges configured to promote interaction between the different agents and the hematopoietic donor cells as the hematopoietic donor cells contact the activation surface, wherein the activation surface comprises a plurality of activation surface regions each including one or more of the different agents, and wherein the activation surface regions are arranged to allow the hematopoietic donor cells to contact each of the activation surface regions with the different agents in a predetermined order to allow multiple steps of activation according to a predetermined activation sequence selected so as to increase expression or activated adhesion molecules including LFA-1 or Mac-1 on the hematopoietic donor cells.

6. The device of claim 5 comprising a container including the surface portion, the container containing the hematopoietic donor cells.

7. The device of claim 6 wherein the container comprises a dish including a bottom portion being the surface portion.

8. The device of claim 6 wherein the container comprises a circular tube having an interior wall to enclose the hematopoietic donor cells, at least a portion of the interior wall being the surface portion.

9. The device of claim 6 comprising a rocker coupled to the container, the rocker adapted to create a motion of the container that causes the hematopoietic donor cells to contact the surface.

10. The device of claim 9 comprising a motion controller coupled to the rocker, the motion controller adapted to control the motion of the container and including:
    a velocity controller to control a velocity of the motion of the container; and
    a pattern controller to control a pattern of the motion of the container.

11. The device of claim 5 comprising an elongate tube including a lumen configured to allow passage of the hematopoietic donor cells, at least a portion of the lumen including the surface portion.

12. The device of claim 11 comprising an injection device configured to deliver the hematopoietic donor cells in the cell therapy, the injection device including the elongate tube.

13. The device of claim 11 comprising:
    a pump coupled to the elongate tube, the pump adapted to pump the hematopoietic donor cells through the lumen; and
    a pump controller coupled to the pump, the pump controller adapted to control a speed of the passage of the hematopoietic donor cells through the lumen.

14. The device of claim 5 comprising a fluid circulating system including:
    a container to contain the hematopoietic donor cells in a fluid; and
    a circulation pathway configured to allow passage of the hematopoietic donor cells and the fluid, the circulation pathway including:
    an entrance to allow the hematopoietic donor cells and the fluid to enter the circulation pathway from the container;
    an exit to allow the hematopoietic donor cells and the fluid to return to the container from the circulation pathway;
    a pump between the entrance and the exit, the pump adapted to pump the hematopoietic donor cells and the liquid through the circulation pathway; and
    the surface portion between the entrance and the exit.

15. The device of claim 14 further comprising a cell delivery system, and wherein the container is a reservoir of the cell delivery system.

16. The device of claim 14 comprising a pump controller to control a speed of movement of the hematopoietic donor cells through the circulation pathway.

17. The device of claim 14 wherein the circulation pathway comprises a tube having an opening being the entrance and a lumen to allow the passage of the hematopoietic donor cells and the fluid, and at least a portion of the lumen includes the surface portion.

18. The device of claim 14 wherein the circulation pathway comprises:
    a tube having an opening being the entrance and a lumen to allow the passage of the hematopoietic donor cells and the fluid; and
    a chamber connected to the tube, the chamber including an interior wall, at least a portion of the interior wall including the surface portion.

19. The device of claim 1 wherein one of the one or more agents applied to the surface portion is a cytokine.

20. The device of claim 1 wherein the one or more agents are applied to the surface portion via a linker.

21. The device of claim 5 wherein the expression or activation of PSGL-1, VLA-4 or L-selectin is increased.

22. The device of claim 5 wherein the hematopoietic cells are progenitor cells.

23. A device for treating progenitor donor cells used in cell therapy, comprising:
    a surface portion; and
    an activation surface including different agents applied to the surface portion, wherein the different agents increase expression or activation of adhesion molecules on progenitor donor cells, the activation surface having ridges configured to promote interaction between the different agents and the progenitor donor cells as the progenitor donor cells contact the activation surface, wherein the activation surface comprises a plurality of activation surface regions each including one or more of the different agents, and wherein the activation surface regions are arranged to allow the progenitor donor cells to contact each of the activation surface regions with the different agents in a predetermined order to allow multiple steps of activation according to a predetermined activation sequence selected so as to increase expression or activated adhesion molecules including LFA-1 or Mac-1 on the progenitor donor cells.

* * * * *